United States Patent [19]

Gyuris et al.

[11] Patent Number: 5,756,671
[45] Date of Patent: May 26, 1998

[54] CDC37 CELL-CYCLE REGULATORY PROTEIN, AND USES RELATED THERETO

[75] Inventors: Jeno Gyuris, Winchester; Lou Lamphere, Boston, both of Mass.; Giulio Draetta, Milan, Italy

[73] Assignee: Mitotix, Inc., Cambridge, Mass.

[21] Appl. No.: 625,209

[22] Filed: Apr. 1, 1996

Related U.S. Application Data

[63] Continuation-in-part of Ser. No. 466,679, Jun. 6, 1995, abandoned, which is a continuation-in-part of Ser. No. 253,155, Jun. 2, 1994, Pat. No. 5,691,147.

[51] Int. Cl.$^6$ .................................................. C07K 14/00

[52] U.S. Cl. .......................................... 530/350; 530/300

[58] Field of Search ................................... 530/350, 300

[56] References Cited

PUBLICATIONS

Ngo et al. In The Protein Foling Problem and Tertiary Structure Production (1994), Merz et al (ed.) Birkhauser, Boston, MA pp. 433, 452–455.

*Primary Examiner*—Stephen Walsh
*Assistant Examiner*—Kenneth A. Sorensen
*Attorney, Agent, or Firm*—Foley, Hoag & Eliot LLP; Matthew P. Vincent, Esq.; Beth E. Arnold, Esq.

[57] ABSTRACT

The present invention relates to the discovery in mammalian cells, particularly human cells, of a novel CDK-binding protein, referred to herein as "cdc37". As described herein, this protein functions to facilitate activation and accordingly functions in the modulation of cell-cycle progression, and therefore ultimately of cell growth and differentiation. Moreover, binding data indicated that cdc37 may function coordinately with other cell-cycle regulatory proteins, such as of cyclin-dependent kinases (CDKs), src, p53 and erk kinases.

37 Claims, 1 Drawing Sheet

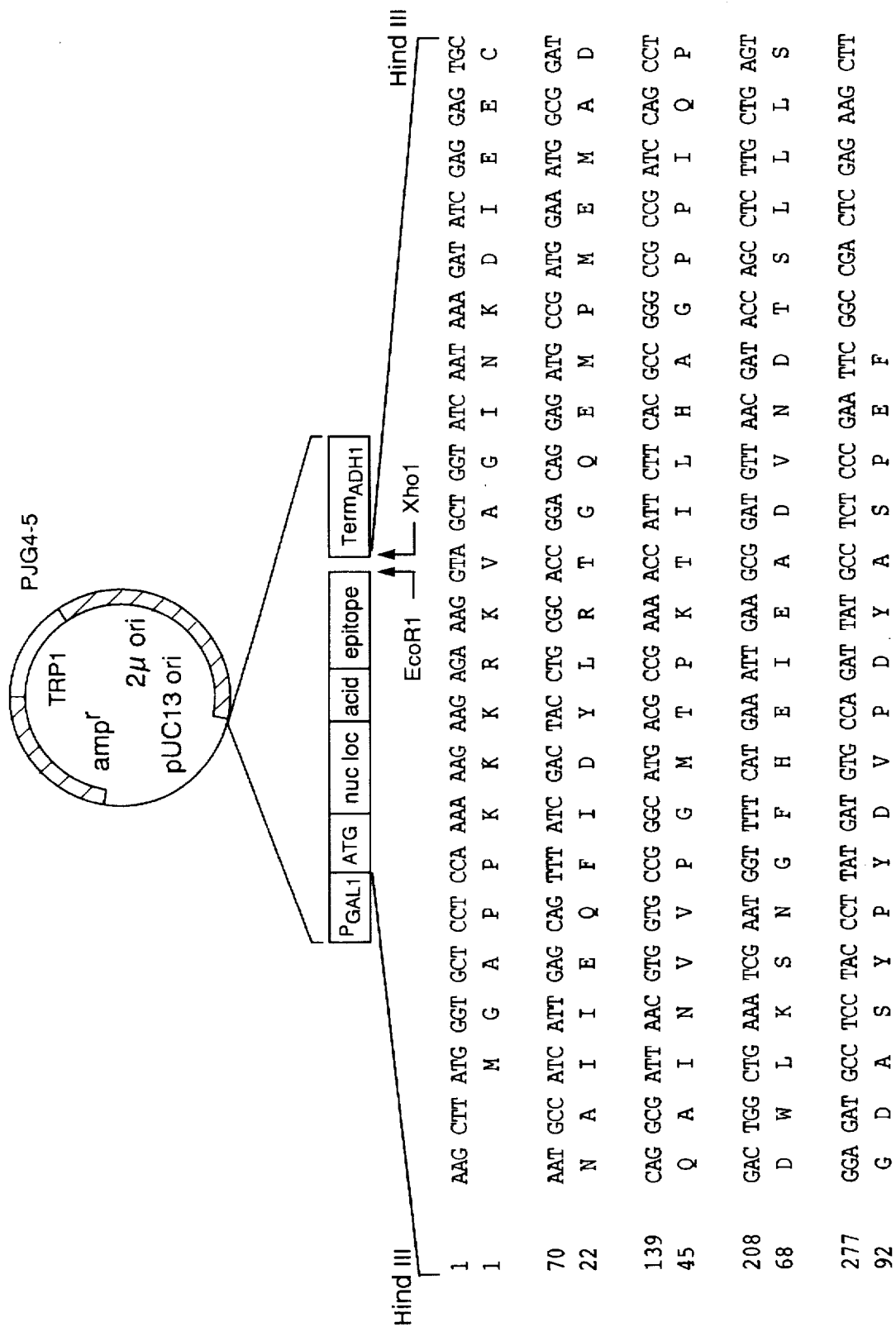

CDC37 CELL-CYCLE REGULATORY PROTEIN, AND USES RELATED THERETO

RELATED APPLICATIONS

This application is a continuation-in-part of U.S. Ser. No. 08/466,679 filed Jun. 6, 1995, now abandoned, entitled "Cdc37 Cell-Cycle Regulatory Protein and Uses Related Thereto", which is a continuation-in-part of U.S. Ser. No. 08/253,155 filed Jun. 2, 1994, now U.S. Pat. No. 5,651,147, entitled "CDK4 Binding Proteins". The teachings of both U.S. Ser. Nos. 08/253,155 and 08/466,679 now abandoned are incorporated herein by reference.

BACKGROUND OF THE INVENTION

Passage of a mammalian cell through the cell cycle is regulated at a number of key control points. Among these are the points of entry into and exit from quiescence ($G_0$), the restriction point, the $G_1$/S transition, and the $G_2$/M transition (for review, see Draetta (1990) *Trends Biol. Sci.* 15:378–383; and Sherr (1993) *Cell* 73:1059–1065). For a cell to pass through a control point and enter the next phase of the cell cycle, it must complete all of the events of the preceding cell cycle phase and, in addition, satisfy a number of check-point controls. Such controls act, for example, to ensure that DNA replication has been successfully completed before the onset of mitosis. Ultimately, information from these check-point controls is integrated through the regulated activity of a group of related kinases, the cyclin-dependent kinases (CDKs). Once a phase of the cell cycle has been successfully completed, phosphorylation of a critical substrates by activated CDKs allow passage of a cell cycle transition point and execution of the next cell cycle phase.

The ordered activation of the different CDKs constitutes the basic machinery of the cell cycle. The activity of CDKs is controlled by several mechanisms that include stimulatory and inhibitory phosphorylation events, and complex formation with other proteins. To become active, CDKs require the association of a group of positive regulatory subunits known as cyclins (see, for example, Nigg (1993) *Trends Cell Biol.* 3:296). In particular, human CDK4 exclusively associates with the D-type cyclins (D1, D2, and D3) (Xiong et al. (1992) *Cell* 71:505; Xiong et al. (1993) *Genes and Development* 7:1572; and Matsushime et al. (1991) *Cell* 65:701) and, conversely, the predominant catalytic partner of the D-type cyclins is the CDK4 kinase (Xiong et al. (1992) *Cell* 71:505). The complexes formed by CDK4 and the D-type cyclins have been strongly implicated in the control of cell proliferation during the G1 phase (Motokura et al. (1993) *Biochem. Biophys. Acta.* 1155:63–78; Sherr (1993) *Cell* 73:1059–1065; Matsushimi et al. (1992) *Cell* 71:323–334); and Kamb et al. (1994) *Science* 264:436–440).

SUMMARY OF THE INVENTION

The present invention relates to the discovery in mammalian cells, particularly human cells, of a novel CDK-binding protein, referred to herein as "cdc37". As described herein, this protein functions to facilitate activation and accordingly functions in the modulation of cell-cycle progression, and therefore ultimately of cell growth and differentiation. Moreover, binding data indicated that cdc37 may function coordinately with other cell-cycle regulatory proteins, such as of cyclin-dependent kinases (CDKs), src, p53 and erk kinases.

One aspect of the invention features a substantially pure preparation of cdc37 polypeptide, or a fragment thereof, the full-length form of the cdc37 protein having an approximate molecular weight in the range of 40–50 kD, preferably about 46 kD. In a preferred embodiment: the polypeptide has an amino acid sequence at least 70% homologous to the amino acid sequence represented in SEQ. ID No. 2; the polypeptide has an amino acid sequence at least 80% homologous to the amino acid sequence represented in SEQ. ID No. 2; the polypeptide has an amino acid sequence at least 90% homologous to the amino acid sequence represented in SEQ. ID No. 2; the polypeptide has an amino acid sequence identical to the amino acid sequence represented in SEQ. ID No. 2. In preferred embodiments: the fragment comprises at least 25 contiguous amino acid residues of SEQ. ID No. 2; the fragment comprises at least 50 contiguous amino acid residues of SEQ. ID No. 2; the fragment comprises at least 75 contiguous amino acid residues of SEQ. ID No. 2.

Polypeptides referred to herein as cdc37 polypeptides preferably have an amino acid sequence corresponding to all or a portion of the amino acid sequence shown in SEQ. ID No. 2, or homologs of this proteins, such other human paralogs, or other mammalian orthologs. In general, the biological activity of a cdc37 polypeptide will be characterized as including the ability to bind to a cyclin-dependent kinase (CDK), preferably CDK4 or CDK6. The above notwithstanding, the biological activity of a cdc37 polypeptide may be characterized by one or more of the following attributes: an ability to regulate the cell-cycle of a mammalian cell, e.g., of a human cell; an ability to modulate proliferation/cell growth of a mammalian cell; an ability to modulate progression of a mammalian cell from G1 phase into S phase; an ability to modulate the kinase activity of a cyclin-dependent kinase, e.g. a CDK active in G1 phase, e.g. CDK4 and/or CDK6. Such activities may be manifest in an ability to modulate phosphorylation of a retinoblastoma (RB) or retinoblastoma-like protein by a CDK. Moreover, the activity of a cdc37 polypeptide of the present invention may also be characterized by: an effect the growth rate of a tumor, e.g. of a tumor having an unimpaired RB protein; an ability to regulate cell-cycle progression in response to extracellular factors and cytokines, e.g. functional in paracrine or autocrine regulation of cell growth and/or differentiation. In this respect, the cdc37 polypeptides of the present invention may also function to modulate differentiation of cells/tissue. The subject polypeptide may also be capable of modulating cell growth or proliferation by influencing the action of other cellular proteins, such as src or p53. The subject polypeptide can also be characterized by an ability to bind to an extracellular-signal regulated kinase (erk), such as erk1 or erk2. A cdc37 polypeptide can be a specific agonist of the function of the wild-type form of the protein, or can be a specific antagonist.

Yet another aspect of the present invention concerns an immunogen comprising a cdc37 polypeptide of the present invention, or a fragment thereof, in an immunogenic preparation, the immunogen being capable of eliciting an immune response specific for the cdc37 polypeptide; e.g. a humoral response, e.g. an antibody response; e.g. a cellular response.

Another aspect of the present invention features recombinant cdc37 polypeptides, or fragments thereof, having amino acid sequences preferably identical or homologous to the amino acid sequence designated by SEQ. ID No. 2.

In yet other preferred embodiments, the recombinant cdc37 polypeptide is a fusion protein further comprising a second polypeptide portion having an amino acid sequence from a protein unrelated the protein of SEQ. ID No. 2. Such fusion proteins can be functional in a two-hybrid assay.

Another aspect of the present invention provides a substantially pure nucleic acid having a nucleotide sequence which encodes a cdc37 polypeptide, or a fragment thereof, having an amino acid sequence at least 70% homologous to one of SEQ. ID Nos. 2. In a more preferred embodiment: the nucleic acid encodes a protein having an amino acid sequence at least 80% homologous to SEQ. ID No. 2, more preferably at least 90% homologous to SEQ. ID No. 2, and most preferably at least 95% homologous to SEQ. ID No. 2. The nucleic preferably encodes a cdc37 protein which specifically binds a cyclin-dependent kinase (CDK), e.g. specifically binds CDK4 and/or CDK6, a gene product of the src proto-oncogene (cellular or viral) and/or p53.

In another embodiment, the nucleic acid hybridizes under stringent conditions to a nucleic acid probe corresponding to at least 25 consecutive nucleotides of SEQ. ID No. 1; more preferably to at least 50 consecutive nucleotides of SEQ. ID No. 1; more preferably to at least 75 consecutive nucleotides of SEQ. ID No. 1.

Furthermore, in certain embodiments, the cdc37 nucleic acid will comprise a transcriptional regulatory sequence, e.g. at least one of a transcriptional promoter or transcriptional enhancer sequence, operably linked to the cdc37 gene sequence so as to render the recombinant cdc37 gene sequence suitable for use as an expression vector.

The present invention also features transgenic non-human animals, e.g. mice, which either express a heterologous cdc37 gene, e.g. derived from humans, or which mis-express their own cdc37 gene, e.g. expression is disrupted. Such a transgenic animal can serve as an animal model for studying cellular disorders comprising mutated or mis-expressed cdc37 alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ. ID No. 1, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a cdc37 encoding nucleic acid in a sample of cells isolated from a patient; e.g. for measuring the mRNA level in a cell or determining whether the genomic cdc37 gene has been mutated or deleted.

The present invention also provides a method for treating an animal having unwanted cell growth characterized by a loss of cell-cycle regulation, comprising administering a therapeutically effective amount of an agent able to inhibit a interaction between a CDK, e.g. CDK4 or CDK6, and cdc37. Likewise, agents which disrupt the binding of an erk protein to cdc37 can also be used to modulate cell proliferation and/or growth. In one embodiment, the method comprises administering a cdc37 mimetic, e.g. a peptidomimetic, which binds to one or more of a CDK or an erk kinase, and inhibits the interaction between that protein and cdc37. Similarly, the present invention contemplates a method for treating an animal having unwanted cell growth characterized by a loss of cell-cycle regulation, comprising administering a therapeutically effective amount of an agent able to inhibit an interaction between cdc37 and a product of the src oncogene (c-src or v-src) or a product of the p53 gene.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a cdc37 gene encoding a protein represented by SEQ. ID No. 2, or a homolog thereof; or (ii) the mis-expression of the cdc37 gene. In preferred embodiments: detecting the genetic lesion comprises ascertaining the existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messenger RNA transcript of said gene, the presence of a non-wild type splicing pattern of a messenger RNA transcript of said gene, or a non-wild type level of said protein. For example, detecting the genetic lesion can comprise (i) providing a probe/primer comprising an oligonucleotide containing a region of nucleotide sequence which hybridizes to a sense or antisense sequence of SEQ. ID No. 1, or naturally occurring mutants thereof, or 5' or 3' flanking sequences naturally associated with the cdc37 gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the cdc37 gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of said protein is detected in an immunoassay.

Yet another aspect of the invention pertains to a CDK4- or CDK6-derived peptidomimetic which binds to the cdc37 protein, and inhibits its binding to a CDK, e.g. CDK4. Likewise, the present invention specifically contemplates cdc37-derived peptidomimetics which bind to CDK4 and inhibit binding of the naturally-occurring cdc37 protein. Non-hydrolyzable peptide analogs of fragments of the cdc37 residues can be generated using, for example, benzodiazepine, azepine, substituted gama lactam rings, ketomethylene pseudopeptides, β-turn dipeptide cores, or β-aminoalcohols. In one embodiment, the peptidomimetic corresponds to the the peptide sequence IYSYQMALT(S/P)V, either in complete sequence, or a portion thereof (e.g., 4, 5 or 6 contiguous residues thereof).

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press, 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning*

(1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

DESCRIPTION OF THE DRAWINGS

FIG. 1 illustrates the pJG4-5 library plasmid and the invariant 107 amino acid moiety it encodes. This moiety (SEQ. ID Nos. 25 and 26) carries (amino to carboxy termini) an ATG, an SV40 nuclear localization sequence (PPKKKRKVA), the B42 transcription activation domain, and the HA1 epitope tag (YPYDVPDYA). pJG4-5 directs the synthesis of proteins under the control of the GAL1 promoter. It carries a 2μ replicator and a TRP1+ selectable marker. Each of the CDK4 binding proteins of ATCC deposit accession number ATCC 75788 are inserted as EcoRI-XhoI fragments. Downstream of the XhoI site, pJG4-5 contains the ADH1 transcription terminator.

DETAILED DESCRIPTION OF THE INVENTION

The division cycle of eukaryotic cells is regulated by a family of protein kinases known as the cyclin-dependent kinases (CDKs). The sequential activation of individual members of this family and their consequent phosphorylation of critical substrates promotes orderly progression through the cell cycle. The complexes formed by the cyclin-dependent kinase 4 (CDK4) and the D-type cyclins, for example, have been strongly implicated in the control of cell proliferation during the G1 phase, and are strong candidates for oncogenes that could be major factors in tumorigenesis. Indeed, recent evidence suggests the possibility that CDK4 may serve as a general activator of cell division in most, if not all, cells.

As described in the appended examples and in parent application U.S. Ser. No. 08/253,155, a CDK4-dependent interaction trap assay (ITS) was used to identify proteins that can associate with human CDK4. The present invention, as set out below, derives from the discovery that, in addition to cyclins, p21, p16, and PCNA, CDK4 is also associated with several other cellular proteins (hereinafter termed "CDK4-binding proteins" or "CDK4-BPs"), which associations are important to the regulation of cell growth, cell proliferation, and/or cell differentiation. Given the central role of CDK4 early in G1 phase, the present data suggest that CDK4 is an important multiplex receiver of signal transduction data, with multiple pathways converging on it to control various aspects of the kinases's activity, including both catalytic activity and substrate specificity. Thus, because each of the proteins identified by the subject ITS act close to the point of CDK4 process control, such as by channeling converging upstream signals to CDK4 or demultiplexing the activation of the CDK4 kinase activity by directing divergent downstream signal propagation from CDK4, each protein is a potential therapeutic target for agents capable of modulating cell proliferation and/or differentiation.

In particular, the present application is directed to the association between CDK4 and a novel human protein which we identified as the mammalian homolog of the yeast gene Cdc37, (though only about 14 percent homologous) the mammalian gene being referred to herein as "cdc37". The present invention, therefore, makes available novel assays and reagents for therapeutic and diagnostic uses. Moreover, drug discovery assays are provided for identifying agents which can affect the binding of cdc37 with a cyclin-dependent kinase or other CDK-associated protein. Such agents can be useful therapeutically to alter, for example, the growth and/or differentiation a cell.

Studies of the temperature-sensitive Cdc37-1 mutant in *Saccharonyces cerevisiae* suggests that Cdc37 is required for exit from G1 phase of the cell-cycle (Reed (1980) *Genetics* 95:561–577; and Ferguson et al. (1986) *Nuc Acid Res* 14:6681–6697). Mutation or deletion in yeast of the Cdc37 gene results in arrest at "START", the regulatory point in the yeast cell-cycle which in many ways resembles the $G_1$ restriction point and $G_1/S$ checkpoint in mammalian cells.

While the precise function of Cdc37 in yeast is not known, our observation of the human cdc37 binding to CDK4 and CDK6 provides an explanation for the $G_1$ phase arrest in Cdc37-1 mutant yeast cells, and also for the role of cdc37 in mammalian cells. It is asserted herein that the mammalian cdc37, and presumably the yeast Cdc37, is required for activation of cyclin-dependent kinases. The cdc37 gene product may be required for stabilization or localization of CDKs such as CDK4, or may play a more general role in the regulation of the kinase activity, such as through allosteric regulation or a chaperon-like activity which facilitates assembly of multi-protein complexes with a CDK. While not wishing to be bound by any particular theory, our results in recombinant expression systems indicate that a transient complex is formed between, for example, CDK4, cyclin $D_1$ and cdc37, with cdc37 dissociating upon phosphorylation of CDK4 by a CDK-activating kinase (CAK).

Futhermore, we have observed that the cdc37 protein itself is apparently regulated, at least in part, by phosphorylation, the phosphorylated form evidently mediating the interaction of, for example, CDK4 and cyclin D1. Using immobilized cdc37, several proteins which bind to cdc37 were purified, e.g. by cdc37 chromatography. Detecting phosphorylation of a cdc37 substrate, a kinase activity was eluted from the cdc37 column under a salt gradiant. The active fractions were pooled, and separated by gel electrophoresis, and an in-gel kinase assay was performed. Five bands were identified in the gel as having kinase activity towards cdc37. Two of the five bands appeared as a doublet, each having a molecular weight of approximately 40 kd. This pattern has been observed previously in the literature for various members of the erk kinase family (for review, see Cobb et al. (1994) *Semin Cancer Biol* 5:261–8), which kinases are involved in signal transduction, especially from mitogenic signals. For instance, transforming agents utilize this cascade in inducing cell proliferation. Indeed, western blot analysis revealed that these two kinase bands isolated by cdc37 binding were the erk-1 and erk-2 kinases, and immunopurified forms of each of these serine/threonine kinases was found to phosphorylate (and activate) cdc37.

Thus, it is understood by the present invention that the human cdc37 functions to control cell-cycle progression, perhaps by integrating extracellular stimulus into cell-cycle control, and it is therefore expected that the CDK4-cdc37, CDK6-cdc37 and erk-cdc37 interactions can be a very important target for drug design. For instance, agents which disrupt the binding of a CDK and cdc37, e.g., CDK4 peptidomimetic which bind cdc37, could be used to effect the progression of cell through G$_1$. Moreover, antagonistic mutants of the subject cdc37 protein, e.g., mutants which disrupt the function of the normal cdc37 protein, can be provided by gene therapy in order to inhibit proliferation of cells. Furthermore, the fact that the human cdc37 homolog37 in cell-cycle checkouts the role of cdc37 in cell-cycle checkpoints, as well as suggesting alternate therapeutic targets, e.g., the Src-cdc37 or p53-cdc37 interactions.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a cdc37 polypeptide of the present invention, including both exon and (optionally) intron sequences. A "recombinant gene" refers to nucleic acid encoding a cdc37 polypeptide and comprising cdc37-encoding exon sequences, though it may optionally include intron sequences which are either derived from a chromosomal cdc37 gene or from an unrelated chromosomal gene. An exemplary recombinant gene encoding the subject cdc37 is represented by SEQ. ID No: 1. The term "intron" refers to a DNA sequence present in a given cdc37 gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a cdc37 polypeptide of the present invention or where anti-sense expression occurs from the transferred gene, the expression of a naturally-occurring form of the cdc37 protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant cdc37 gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the cdc37 protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of cdc37, e.g. either agonistic or antagonistic forms. However, transgenic animals in which the recombinant cdc37 gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis and tissue patterning. The term "chimeric animal" is used herein to refer to animals in which the recombinant gene is found, or in which the recombinant is expressed in some but not all cells of the animal. The term "tissue-specific chimeric animal" indicates that the recombinant cdc37 gene is present and/or expressed in some tissues but not others.

As used herein, the term "transgene" means a nucleic acid sequence (encoding, e.g., a cdc37 polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a cdc37 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding the subject cdc37 polypeptide with a second amino acid sequence defining a domain foreign to and not substantially homologous with any domain of the cdc37 polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "evolutionarily related to", with respect to nucleic acid sequences encoding cdc37, refers to nucleic acid sequences which have arisen naturally in an organism, including naturally occurring mutants. The term also refers to nucleic acid sequences which, while derived from a naturally occurring cdc37 genes, have been altered by mutagenesis, as for example, combinatorial mutagenesis described below, yet still encode polypeptides which have at least one activity of a cdc37.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding the subject cdc37 polypeptides preferably include no more than 10 kilobases (kb) of nucleic acid sequence which naturally immediately flanks particular cdc37 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to an isolated nucleic acid having a nucleotide sequence encoding a cdc37 protein, and/or equivalents of such nucleic acids. The term nucleic acid as used herein is intended to include fragments and equivalents. The term equivalent is understood to include nucleotide sequences encoding functionally equivalent cdc37 proteins or functionally equivalent polypeptides which, for example, retain the ability to bind to a cyclin-dependent kinase. Equivalent nucleotide sequences will include sequences that differ by one or more nucleotide substitutions, additions or deletions, such as allelic variants; and will, therefore, include sequences that differ from the nucleotide sequence of the cdc37 gene shown in SEQ. ID No: 1 due to the degeneracy of the genetic code. Equivalents will also include nucleotide sequences that hybridize under stringent conditions (i.e., equivalent to about 20°–27° C. below the melting temperature ($T_m$) of the DNA duplex formed in about 1M salt) to the nucleotide sequence of cdc37 gene represented in SEQ. ID No: 1. In one embodiment, equivalents will further include nucleic acid sequences derived from and evolutionarily related to, a nucleotide sequences shown in SEQ. ID No: 1.

Moreover, it will be generally appreciated that, under certain circumstances, it may be advantageous to provide homologs of the subject cdc37 protein, which homologs function in a limited capacity as one of either an agonists (mimetic) or an antagonist of cdc37 activity, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of cdc37s biological activities. For instance, antagonistic homologs can be generated which interfere with the ability of the wild-type ("authentic") cdc37 protein to form complexes with CDK4, but which do not substantially interfere with the formation of complexes between cdc37 and CDK6 or other cellular proteins, such as may be involved in other regulatory mechanisms of the cell.

Polypeptides referred to herein as cdc37 polypeptides preferably have an amino acid sequence corresponding to all or a portion of the amino acid sequence shown in SEQ. ID No. 2, or homologs of this proteins, such other human paralogs, or other mammalian orthologs. In general, the biological activity of a cdc37 polypeptide will be characterized as including the ability to bind to a cyclin-dependent kinase (CDK), preferably CDK4. The above notwithstanding, the biological activity of a cdc37 polypeptide may be characterized by one or more of the following attributes: an ability to regulate the cell-cycle of a mammalian cell, e.g., of a human cell; an ability to modulate proliferation/cell growth of a mammalian cell; an ability to modulate progression of a mammalian cell from G1 phase into S phase; an ability to modulate the kinase activity of a cyclin-dependent kinase, e.g. a CDK active in G1 phase, e.g. CDK4. Such activities may be manifest in an ability to modulate phosphorylation of a retinoblastoma (RB) or retinoblastoma-like protein by a CDK. Moreover, the activity of a cdc37 polypeptide of the present invention may also be characterized by: an effect the growth rate of a tumor, e.g. of a tumor having an unimpaired RB protein; an ability to regulate cell-cycle progression in response to extracellular factors and cytokines, e.g. functional in paracrine or autocrine regulation of cell growth and/or differentiation. In this respect, the cdc37 polypeptides of the present invention may also function to modulate differentiation of cells/tissue. Other biological activities of the subject cdc37 proteins are described herein, such as an ability to a particular protein, e.g., an erk kinase, p53 or src, or will be reasonably apparent to those skilled in the art in light of the present disclosure.

In one embodiment, the nucleic acid of the invention encodes a polypeptide which is an agonist or antagonist of the naturally occurring cdc37 protein and comprises an amino acid sequence identical or homologous to the amino acid sequence represented in SEQ. ID No. 2. Preferred nucleic acids encode a polypeptide at least 60% homologous, more preferably 70% homologous and most preferably 80% homologous with an amino acid sequence shown in SEQ. ID No. 2. Nucleic acids which encode polypeptides having an activity of a cdc37 protein and having at least about 90%, more preferably at least about 95%, and most preferably at least about 98–99% homology with a sequence shown in SEQ. ID No 2 are also within the scope of the invention. Preferably, the nucleic acid is a cDNA molecule comprising at least a portion of the nucleotide sequence encoding a cdc37 protein shown in SEQ. ID No. 2. A preferred portion of the cDNA molecule shown in SEQ. ID No. 1 includes the coding region of the molecule.

Another aspect of the invention provides a nucleic acid which hybridizes under high or low stringency conditions to a nucleic acid which encodes a cdc37 polypeptide having all or a portion of an amino acid sequence shown in SEQ. ID No: 2. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids which, differ from the nucleotide sequences shown in SEQ. ID No: 1 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject cdc37 proteins will exist among mammalian cells. One skilled in the art will appreciate that these variations in one or more nucleotides (up to about 3–4% of the nucleotides) of the nucleic acids encoding a particular member of the cdc37 protein family may exist among individuals of a given species due to natural allelic variation. Any and all such nucleotide variations and resulting amino acid polymorphisms are within the scope of this invention.

Fragments of the nucleic acid encoding a biologically active portion of the subject cdc37 proteins are also within the scope of the invention. As used herein, a fragment of the nucleic acid encoding an active portion of a cdc37 protein refers to a nucleotide sequence having fewer nucleotides than the nucleotide sequence encoding the full length amino acid sequence of, for example, the cdc37 protein represented in SEQ. ID No: 2, and which encodes a polypeptide which retains at least a portion of the biological activity of the full-length protein (i.e., a polypeptide capable of binding a CDK, an erk kinase, or both) as defined herein, or alternatively, which is functional as an antagonist of the biological activity of the full-length protein. Nucleic acid fragments within the scope of the invention include those capable of hybridizing under high or low stringency conditions with nucleic acids from other species, e.g. for use in screening protocols to detect homologs. Nucleic acids within the scope of the invention may also contain linker sequences, modified restriction endonuclease sites and other sequences useful for molecular cloning, expression or purification of such recombinant polypeptides.

As indicated by the examples set out below, a nucleic acid encoding a cdc37 polypeptide may be obtained from mRNA or genomic DNA present in any of a number of mammalian cells in accordance with protocols described herein, as well as those generally known to those skilled in the art. A cDNA encoding a cdc37 polypeptide, for example, can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. A gene encoding a cdc37 protein can also be cloned using established polymerase chain reaction techniques in accordance with the nucleotide sequence information provided by the invention. A preferred nucleic acid is a cDNA encoding a cdc37 protein has a sequence represented in SEQ. ID No. 1.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a cdc37 protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a cdc37 protein. Alternatively, the antisense construct is an oligonucleotide probe which is generated ex vivo and which, when introduced into the cell causes inhibition of expression by hybridizing with the mRNA and/or genomic sequences encoding a cdc37 protein. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of modes of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind.

This invention also provides expression vectors comprising a nucleotide sequence encoding a subject cdc37 polypeptide and operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the polypeptide having an activity of a cdc37 protein. Accordingly, the term regulatory sequence includes promoters, enhancers and other expression control elements. Exemplary regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the cdc37 proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda , the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject cdc37 polypeptides in cells propagated in culture, e.g. to produce proteins or polypeptides, including fusion proteins or polypeptides, for purification. In addition, recombinant expression of the subject cdc37 polypeptides in cultured cells can be useful for controlling differentiation states of cells in vitro, for instance, by controlling the level of activation of a CDK. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. By preventing the activation of a $G_0/G_1$ CDK, certain of the cdc37 homologs (presumably antagonist forms) can prevent mitotic progression and hence provide a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art. In this respect, each of the agonist and antagonist of CDK4 activation can be used for ex vivo tissue generation, as for example, to enhance the generation of prosthetic tissue devices for implantation.

To further illustrate, by antagonizing the activity of the wild-type cdc37 protein, such as by expression of antagonistic homologs, antisense constructs, or treatment with agents able to disrupt binding of a cdc37 protein with, for example, a CDK or an erk kinase the cultured cells can be guided along certain differentiative pathways.

Moreover, antagonizing the activity of the wild-type cdc37 protein, such as by expression of antagonistic homologs, antisense constructs, or treatment with agents able to disrupt binding of a cdc37 protein with a CDK, can be utilized in diagnostic assays to determine if a cell's growth is no longer dependent on the regulatory function of a cdc37 protein, e.g. in determining the phenotype of a transformed cell. To illustrate, a sample of cells from the tissue can be obtained from a patient and dispersed in appropriate cell culture media, a portion of the cells in the sample can be caused to express a dominant negative mutant cdc37 protein, e.g. by transfection with an expression vector, and subsequent growth of the cells assessed. The ability of cells to proliferate despite expression of an antagonistic cdc37 protein is indicative of a lack of dependence on cell regulatory pathways which include the cdc37 protein, e.g. CDK4-dependent pathways such as RB-mediated checkpoints. Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art. Such knowledge can have both prognostic and therapeutic benefits.

This invention also pertains to a host cell transfected with a recombinant cdc37 gene in order to express a polypeptide having an activity of a cdc37 protein. The host cell may be any prokaryotic or eukaryotic cell. For example, a cdc37 protein of the present invention may be expressed in bacterial cells such as *E. coli*, insect cells (baculovirus), yeast, or mammalian cells. Other suitable host cells are known to those skilled in the art.

Another aspect of the present invention concerns recombinant cdc37 proteins which have at least one biological activity of a naturally occurring cdc37 protein, or which are naturally occurring mutants thereof. The term "recombinant protein" refers to a protein of the present invention which is produced by recombinant DNA techniques, wherein generally DNA encoding the cdc37 protein is inserted into a suitable expression vector which is in turn used to transform a host cell to produce the heterologous protein. Moreover, the phrase "derived from", with respect to a recombinant gene encoding the recombinant cdc37 protein, is meant to include within the meaning of "recombinant protein" those proteins having an amino acid sequence of a native cdc37 protein, or an amino acid sequence similar thereto which is generated by mutations including substitutions and deletions of a naturally occurring cdc37 protein. To illustrate, recombinant proteins preferred by the present invention, in addition to native cdc37 proteins, are those recombinantly produced proteins which are at least 60% homologous, more preferably 70% homologous and most preferably 80% homologous with an amino acid sequence shown in SEQ. ID No. 2. Polypeptides having an activity of a cdc37 protein, such as CDK-binding and/or erk-binding, and having at least about 90%, more preferably at least about 95%, and most preferably at least about 98–99% homology with a sequence shown in SEQ. ID No. 2 are also within the scope of the invention. Thus, the present invention pertains to recombinant cdc37 proteins which are encoded by genes derived from a mammal and which have amino acid sequences evolutionarily related to a cdc37 protein represented by one of ID No. 2, wherein "evolutionarily related to", refers to cdc37 proteins having amino acid sequences which have arisen naturally (e.g. by allelic variance or by differential splicing), as well as mutational variants of cdc37 proteins which are derived, for example, by combinatorial mutagenesis.

The present invention further pertains to methods of producing the subject cdc37 proteins. For example, a host cell transfected with an expression vector encoding a cdc37 polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the cdc37 protein. In a preferred embodiment, the cdc37 protein is a fusion protein containing a domain which facilitates its purification, such as a cdc37-GST fusion protein.

Thus, a nucleotide sequence derived from the cloning of a cdc37 protein of the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known cell-cycle regulatory proteins, e.g. p53, cyclins, RB, p16, p21, and the like. Similar procedures, or modifications thereof, can be employed to prepare recombinant cdc37 proteins, or portions thereof, by microbial means or tissue-culture technology in accord with the subject invention.

The recombinant cdc37 protein can be produced by ligating the cloned gene, or a portion thereof, into a vector suitable for expression in either prokaryotic cells, eukaryotic cells, or both. Expression vehicles for production of a recombinant cdc37 protein include plasmids and other vectors. For instance, suitable vectors for the expression of cdc37 include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant cdc37 protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a carboxy terminal fragment of the full-length cdc37 protein is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of the cdc37 protein. For example, the VP6 capsid protein of rotavirus can be used as an immunologic carrier protein for portions of polypeptide, either in the monomeric form or in the form of a viral particle. The nucleic acid sequences corresponding to the portion of the cdc37 protein to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of a cdc37 protein and the poliovirus capsid protein can be created to enhance immunogenicity (see, for example, EP Publication No. 0259149; and Evans et al. (1989) *Nature* 339:385; Huang et al. (1988) *J Virol.* 62:3855; and Schlienger et al. (1992) *J Virol.* 66:2).

The Multiple Antigen Peptide system for peptide-based immunization can be utilized, wherein a desired portion of a cdc37 protein is obtained directly from organo-chemical synthesis of the peptide onto an oligomeric branching lysine core (see, for example, Posnett et al. (1988) *JBC* 263:1719 and Nardelli et al. (1992) *J Immunol.* 148:914). Antigenic determinants of the cdc37 protein can also be expressed and presented by bacterial cells.

In addition to utilizing fusion proteins to enhance immunogenicity, it is widely appreciated that fusion proteins can also facilitate the expression of proteins. For example, the cdc37 protein of the present invention can be generated as a glutathione-S-transferase (GST) fusion proteins. Such GST fusion proteins can be used to simply purification of the cdc37 protein, such as through the use of glutathione-derivatized matrices (see, for example, *Current Protocols in Molecular Biology*, eds. Ausabel et al. (N.Y.: John Wiley & Sons, 1991)).

In another embodiment, a fusion gene coding for a purification leader sequence, such as a poly-(His)/ enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified cdc37 protein (e.g., see Hochuli et al. (1987) *J. Chromatography* 411:177; and Janknecht et al. PNAS 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The present invention also makes available isolated and/ or purified forms of the subject cdc37 polypeptides, which are isolated from, or otherwise substantially free of other intracellular proteins, especially cell-cycle regulatory proteins, e.g. CDKs, cyclins, p16, p21, p19, or PCNA, which might normally be associated with the cdc37 protein. The term "isubstantially free of other cellular proteins" (also referred to herein as "contaminating proteins") is defined as encompassing, for example, cdc37 preparations comprising less than 20% (by dry weight) contaminating protein, and preferably comprises less than 5% contaminating protein. Functional forms of the cdc37 polypeptide can be prepared, for the first time, as purified preparations by using a cloned gene as described herein. By "purified", it is meant, when referring to a polypeptide, that the indicated molecule is present in the substantial absence of other biological macromolecules, such as other proteins (particularly other cell-cycle proteins such as CDK4 or CDK6, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

However, the subject polypeptides can also be provided in pharmaceutically acceptable carriers for formulated for a variety of modes of administration, including systemic and topical or localized administration. Techniques and formulations generally may be found in Remmington's Pharmaceutical Sciences, Meade Publishing Co., Easton, Pa. In an exemplary embodiment, the cdc37 polypeptide is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

Another aspect of the invention related to polypeptides derived from the full-length cdc37 protein. Isolated peptidyl portions of the subject cdc37 protein can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, cdc37 can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, CDK4 activation or erk kinase activity, such as by microinjection assays. In an illustrative embodiment, peptidyl portions of cdc37 can tested for CDK-binding activity, as well as inhibitory ability, by expression as, for example, thioredoxin fusion proteins, each of which contains a discrete fragment of the cdc37 protein (see, for example, U.S. Pat. Nos. 5,270,181 and 5,292,646; and PCT publication WO94/02502).

It is also possible to modify the structure of the subject cdc37 protein for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the cdc37 polypeptides described in more detail herein. Such modified polypeptides can be produced, for instance, by amino acid substitution, deletion, or addition.

Moreover, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resultingmolecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide= asparagine, glutamine; and (6) sulfur-containing=cysteine and methionine. (see, for example, Biochemistry, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of cdc37 can be assessed for their ability to bind to a cyclin-dependent kinase, p53, Src or other cellular protein. Polypeptides in which more than one replacement has taken place can readily be tested in the same manner.

This invention further contemplates a method of generating sets of combinatorial mutants of the present cdc37 proteins, as well as truncation mutants, and is especially useful for identifying potential variant sequences (e.g. homologs) that are finctional in binding to a CDK, especially CDK4. Similar embodiments are contemplated for polypeptides which retain the ability to bind to an erk kinase, e.g. erk1 or erk2. The purpose of screening such combinatorial libraries is to generate, for example, cdc37 homologs which can act as either agonists or antagonist, or alternatively, possess novel activities all together. To illustrate, homologs can be engineered by the present method to provide more efficient binding to CDK4, yet have a significantly reduced binding affinity for other CDKs relative to the naturally-occurring form of the protein. Thus, combinatorially-derived homologs can be generated which have a selective potency relative to a naturally occurring cdc37 protein. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the cdc37 protein. Such homologs, and the genes which encode them, can be utilized to alter the envelope of cdc37 expression by modulating the half-life of the protein. For instance, a short half-life can give rise to more transient biological effects and, when part of an inducible expression system, can allow tighter control of recombinant cdc37 protein levels within the cell. As above, such proteins, and particularly their recombinant nucleic acid constructs, can be used in gene therapy protocols.

In similar fashion, cdc37 homologs can be generated by the present combinatorial approach to act as antagonists, in that they are able to interfere with the ability of the corresponding wild-type protein to regulate cell proliferation.

In a representative embodiment of this method, the amino acid sequences for a population of cdc37 protein homologs are aligned, preferably to promote the highest homology possible. Such a population of variants can include, for example, homologs from one or more species, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential cdc37 protein sequences. For instance, a mixture of synthetic oligonucleotides can be enzymatically ligated into gene sequences such that the degenerate set of potential cdc37 nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential cdc37 sequences. The synthesis of degenerate oligonucleotides is well known in the art (see for example, Narang, SA (1983) Tetrahedron 39:3; Itakura et al. (1981) Recombinant DNA, Proc. 3rd Cleveland Sympos. Macromolecules, ed. AG Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res.

11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos: 5,223,409, 5,198,346, and 5,096,815).

Alternatively, other forms of mutagenesis can be utilized to generate a combinatorial library. For example, cdc37 homologs (both agonist and antagonist forms) can be generated and isolated from a library by screening using, for example, alanine scanning mutagenesis and the like (Ruf et al. (1994) Biochemistry 33:1565–1572; Wang et al. (1994) J. Biol. Chem. 269:3095–3099; Balint et al. (1993) Gene 137:109–118; Grodberg et al. (1993) Eur. J. Biochem. 218:597–601; Nagashima et al. (1993) J. Biol. Chem. 268:2888–2892; Lowman et al. (1991) Biochemistry 30:10832–10838; and Cunningham et al. (1989) Science 244:1081–1085), by linker scanning mutagenesis (Gustin et al. (1993) Virology 193:653–660; Brown et al. (1992) Mol. Cell Biol. 12:2644–2652; McKnight et al. (1982) Science 232:316); by saturation mutagenesis (Meyers et al. (1986) Science 232:613); by PCR mutagenesis (Leung et al. (1989) Method Cell Mol Biol 1:11–19); or by random mutagenesis (Miller et al. (1992) A Short Course in Bacterial Genetics, CSHL Press, Cold Spring Harbor, N.Y.; and Greener et al. (1994) Strategies in Mol Biol 7:32–34). Linker scanning matagenesis, particularly in a combinatorial setting, is on attractive method for identifying truncated (bioactive) forms of the cdc37 protein.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of cdc37 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, the candidate combinatorial gene products are displayed on the surface of a cell, and the ability of particular cells or viral particles to bind a CDK, such as CDK4 or CDK6, or other binding partners of cdc37, e.g., p53 or Src, via this gene product is detected in a "panning assay". For instance, the cdc37 gene library can be cloned into the gene for a surface membrane protein of a bacterial cell (Ladner et al., WO 88/06630; Fuchs et al. (1991) Bio/Technology 9:1370–1371; and Goward et al. (1992) TIBS 18:136–140), and the resulting fusion protein detected by panning, e.g. using a fluorescently labeled molecule which binds the cdc37 protein, e.g. FITC-CDK4, to score for potentially functional homologs. Cells can be visually inspected and separated under a fluorescence microscope, or, where the morphology of the cell permits, separated by a fluorescence-activated cell sorter.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

In an illustrative embodiment, the recombinant phage antibody system (RPAS, Pharmacia Catalog number 27-9400-01) can be easily modified for use in expressing and screening cdc37 combinatorial libraries of the present invention. For instance, the pCANTAB 5 phagemid of the RPAS kit contains the gene which encodes the phage gIII coat protein. The cdc37 combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate cdc37 gene insert. The resulting recombinant phage contain phagemid DNA encoding a specific candidate cdc37 protein, and display one or more copies of the corresponding fusion coat protein. The phage-displayed candidate proteins which are capable of, for example, binding CDK4, are selected or enriched by panning. For instance, the phage library can be panned on glutathione immobilized CDK4-GST fusion proteins, and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for cdc37 homologs which can then be screened for further biological activities in order to differentiate agonists and antagonists.

Consequently, the invention also provides for reduction of the subject cdc37 protein to generate mimetics, e.g. peptide or non-peptide agents, which are able to mimic binding of the authentic cdc37 protein to another cellular partner, e.g. a cyclin-dependent kinase, e.g. CDK4, or other cellular protein, e.g., an erk kinase, p53 or Src. Such mutagenic techniques as described above, as well as the thioredoxin system, are also particularly useful for mapping the determinants of a cdc37 protein which participate in protein-protein interactions involved in, for example, binding of the subject cdc37 protein to CDK4, CDK6, erk1, erk2, Src or p53. To illustrate, the critical residues of a cdc37 protein which are involved in molecular recognition of CDK4 can be determined and used to generate cdc37 derived peptidomimetics which bind to CDK4, and by inhibiting cdc37 binding, act to prevent activation of the kinase. By employing, for example, scanning mutagenesis to map the amino acid residues of cdc37 which are involved in binding CDK4, peptidomimetic compounds (e.g. diazepine or isoquinoline derivatives) can be generated which mimic those residues in binding to the kinase. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71).

Another aspect of the invention pertains to an antibody specifically reactive with a cdc37 protein. For example, by using peptides based on the sequence of the subject cdc37 protein, anti-cdc37 antisera or anti-cdc37 monoclonal antibodies can be made using standard methods. A mammal such as a mouse, a hamster or rabbit can be immunized with an immunogenic form of the peptide (e.g., an antigenic fragment which is capable of eliciting an antibody response). Techniques for conferring inumunogenicity on a protein or peptide include conjugation to carriers or other techniques well known in the art. For instance, a peptidyl portion of the protein represented by SEQ. ID No. 2 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-cdc37 antisera can be obtained and, if desired, polyclonal anti-cdc37 antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), as the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the cdc37 protein and the monoclonal antibodies isolated.

The term antibody as used herein is intended to include fragments thereof which are also specifically reactive with a mammalian cdc37 protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules.

Both monoclonal and polyclonal antibodies (Ab) directed against the subject cdc37 protein, and antibody fragments such as Fab' and F(ab')$_2$, can be used to block the action of cdc37 and allow the study of the cell-cycle or cell proliferation.

Another application of anti-cdc37 antibodies is in the immunological screening of cDNA libraries constructed in expression vectors, such as λgt11, λgt18-23, αZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a cdc37 protein, such as proteins antigenically related to the human cdc37 protein of SEQ. ID No. 2, can then be detected with antibodies, as, for example, reacting nitrocellulose filters lifted from infected plates with an anti-cdc37 antibody. Phage, scored by this assay, can then be isolated from the infected plate. Thus, cdc37 homologs can be detected and cloned from other sources.

Antibodies which are specifically immunoreactive with a cdc37 protein of the present invention can also be used in immunohistochemical staining of tissue samples in order to evaluate the abundance and pattern of expression of the protein. Anti-cdc37 antibodies can be used diagnostically in immuno-precipitation and immuno-blotting to detect and evaluate levels of one or more cdc37 proteins in tissue or cells isolated from a bodily fluid as part of a clinical testing procedure. For instance, such measurements can be useful in predictive valuations of the onset or progression of tumors. Likewise, the ability to monitor certain cdc37 protein levels in an individual can allow determination of the efficacy of a given treatment regimen for an individual afflicted with such a disorder. Diagnostic assays using anti-cdc37 antibodies, can include, for example, immunoassays designed to aid in early diagnosis of a neoplastic or hyperplastic disorder, e.g. the presence of cancerous cells in the sample, e.g. to detect cells in which alterations in expression levels of cdc37 gene has occurred relative to normal cells.

In addition, nucleotide probes can be generated from the cloned sequence of cdc37, which probes will allow for histological screening of intact tissue and tissue samples for the presence of a cdc37-encoding mRNA. Similar to the diagnostic uses of anti-cdc37 protein antibodies, the use of probes directed to cdc37 messages, or to genomic cdc37 gene sequences, can be used for both predictive and therapeutic evaluation of allelic mutations or abnormal transcription which might be manifest, in, for example, neoplastic or hyperplastic disorders (e.g. unwanted cell growth).

Accordingly, the present method provides a method for determining if a subject is at risk for a disorder characterized by unwanted cell proliferation. In preferred embodiments, the method can be generally characterized as comprising detection, in a tissue of the subject, the presence or absence of a genetic lesion manifest as at least one of (i) a mutation of a gene encoding a cdc37 protein, or (ii) the misexpression of the cdc37 gene. To illustrate, such genetic lesions can be detected by ascertaining the existence of at least one of (i) a deletion of one or more nucleotides from a cdc37 gene, (ii) an addition of one or more nucleotides to a cdc37 gene, (iii) a substitution of one or more nucleotides of a cdc37 gene, (iv) a gross chromosomal rearrangement of a cdc37 gene, (v) a gross alteration in the level of a messenger RNA transcript of a cdc37 gene, (vi) the presence of a non-wild type splicing pattern of a messenger RNA transcript of a cdc37 gene, and (vii) a non-wild type level of a cdc37 protein. In one aspect of the invention, there is provided a probe/primer comprising an oligonucleotide containing a region of nucleotide sequence which is capable of hybridizing to a sense or antisense sequence of SEQ. ID No: 1 or naturally occurring mutants thereof, or 5' or 3' flanking sequences or intronic sequences naturally associated with the subject cdc37 gene or naturally occurring mutants thereof. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g. U.S. Pat. Nos. 4,683,195 and 4,683,202), or, alternatively, in a ligation chain reaction (LCR) (see, e.g., Landegran et al. (1988) *Science* 241:1077–1080; and Nakazawa et al. (1944) *PNAS* 91:360–364), the later of which can be particularly useful for detecting point mutations in the cdc37 gene. Alternatively, the level of cdc37 protein can detected in an immunoassay.

Another aspect of the invention features transgenic non-human animals which express a heterologous cdc37 gene of the present invention, or which have had one or more genomic cdc37 gene(s) disrupted in at least one of the tissue or cell-types of the animal. For instance, transgenic mice that are disrupted at their cdc37 gene locus can be generated.

In another aspect, the invention features an animal model for developmental diseases, which has a cdc37 allele which is mis-expressed. For example, a mouse can be bred which has a cdc37 allele deleted, or in which all or part of one or more cdc37 exons are deleted. Such a mouse model can then be used to study disorders arising from mis-expression of the cdc37 gene.

Accordingly, the present invention concerns transgenic animals which are comprised of cells (of that animal) which contain a transgene of the present invention and which preferably (though optionally) express an exogenous cdc37 protein in one or more cells in the animal. The cdc37 transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of the subject protein can be essential for many forms of lineage analysis and can additionally provide a means to assess the effects of, for example, modulation of activation of CDK4 which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject cdc37 polypeptide. For example, excision of a target sequence which interferes with the expression of a recombinant cdc37 gene can be designed to activate expression of that gene. This interference with expression of the protein can result from a variety of mechanisms, such as spatial separation of the cdc37 gene from the promoter element or an internal stop codon. Moreover, the transgene can be made wherein the coding sequence of the gene is flanked recombinease6mbinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the cdc37 gene can be regulated via regulation of recombinase expression.

Use of the cre/loxP recombinase system to regulate expression of a recombinant cdc37 protein requires the construction of a transgenic animal containing transgenes encoding both the Cre recombinase and the subject protein. Animals containing both the Cre recombinase and the recombinant cdc37 genes can be provided through the construction of "double" transgenic animals. A convenient method for providing such animals is to mate two transgenic animals each containing a transgene, e.g., the cdc37 gene and recombinase gene.

One advantage derived from initially constructing transgenic animals containing a cdc37 transgene in a recombinase-mediated expressible formnat derives from the likelihood that the subject protein may be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic cdc37 transgene is silent will allow the study of progeny from that founder in which disruption of cell-cycle regulation in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the cdc37 transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a cdc37 gene can be controlled as above.

Yet another aspect of the invention pertains to methods of treating proliferative and/or differentiative disorders which arise from cells which, despite aberrant growth control, still require a cdc37-dependent CDK for cell growth. There are a wide variety of pathological cell proliferative conditions for which the cdc37 gene constructs, cdc37 mimetics, and cdc37 antagonists of the present invention can provide therapeutic benefits, with the general strategy being the inhibition of anomalous cell proliferation. For instance, the gene constructs of the present invention can be used as a part of a gene therapy protocol, such as to reconstitute the function of a cdc37 protein, e.g. in a cell in which the protein is misexpressed or in which signal transduction pathways upstream of the cdc37 protein are dysfunctional, or to inhibit the function of the wild-type protein, e.g. by delivery of a dominant negative mutant.

To illustrate, cell types which exhibit pathological or abnormal growth presumably dependent at least in part on a function of a cdc37 protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from either de-differentiation of tissue due to aberrant reentry into mitosis, or unwanted differentiation due to a failure to appropriately activate certain CDK complexes.

It will also be apparent that, by transient use of gene therapy constructs of the subject cdc37 proteins (e.g. agonist and antagonist forms) or antisense nucleic acids, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, cdc37 agonists and antagonists can be employed therapeutically to regulate organs after physical, chemical or pathological insult. For example, gene therapy can be utilized in liver repair subsequent to a partial hepatectomy, or to promote regeneration of lung tissue in the treatment of emphysema.

In one aspect of the invention, expression constructs of the subject cdc37 proteins may be administered in any biologically effective carrier, e.g. any formulation or composition capable of effectively transfecting cells in vivo with a recombinant cdc37 gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g.

antibody conjugated), polylysine conjugates, gramacidin S, artificial viral envelopes or other such intracellular carriers, as well as direct injection of the gene construct or CaPO₄ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a cdc37 polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject cdc37 genes, it is important to note that a prerequisite for the successful infection of target cells by most retroviruses, and therefore of stable introduction of the recombinant cdc37 gene, is that the target cells must be dividing. In general, this requirement will not be a hindrance to use of retroviral vectors to deliver antagonistic cdc37 gene constructs. In fact, such limitation on infection can be beneficial in circumstances wherein the tissue (e.g. nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface ligands to the viral env proteins (Neda et al. (1991) *J. Biol. Chem.* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the cdc37 gene of the retroviral vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) *BioTechniques* 6:616; Rosenfeld et al. (1991) *Science* 252:431–434; and Rosenfeld et al. (1992) *Cell* 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7, pp. 109–127). Expression of the inserted cdc37 gene can be under control of, for example, the E1A promoter, the major late promoter (MLP) and associated leader sequences, the E3 promoter, or exogenously added promoter sequences.

Yet another viral vector system useful for delivery of the subject cdc37 gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant cdc37 gene in cells of the central nervous system and ocular tissue (Pepose et al. (1994) *Invest Ophthalmol Vis Sci* 35:2662–2666)

In addition to viral transfer methods, such as those illustrated above, non-viral methods can also be employed to cause expression of a cdc37 protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject cdc37 gene by the targeted cell. Exemplary gene delivery systems of this type include liposomal derived systems, poly-lysine conjugates, and artificial viral envelopes.

In a representative embodiment, a gene encoding a cdc37 polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO01/06309; Japanese patent application 1047381; and European patent publication EP-A-43075). For example, lipofection of neuroglioma cells can be carried out using liposomes tagged with monoclonal antibodies against glioma-associated antigen (Mizuno et al. (1992) *Neurol. Med. Chir.* 32:873–876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, the subject cdc37 gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via -mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260–926; Wagner et al. (1992) *PNAS* 89:7934; and Christiano et al. (1993) *PNAS* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical &*

*Dental Materials*, ed. by David Williams (MIT Press: Cambridge, Mass., 1990); and the Sabel et al. U.S. Pat. No. 4,883,666. In another embodiment of an implant, a source of cells producing a the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the viral packaging cells (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotechnol Bioeng.* 29:1135–1143; and Aebischer et al. (1991) *Biomaterials* 12:50–55). Again, manipulation of the polymer can be carried out to provide for optimal release of viral particles.

As set out above, the present invention also provides assays for identifying drugs which are either agonists or antagonists of the normal cellular function of cdc37, or of the role of cdc37 in the pathogenesis of normal or abnormal cellular proliferation and/or differentiation and disorders related thereto, as mediated by, for example binding of cdc37 to a target protein, e.g., CDK4, CDK6, an erk kinase, Src or p53. In one embodiment, the assay evaluates the ability of a compound to modulate binding of cdc37 to a CDK or other of cell-cycle regulatory protein. While the following description is directed generally to embodiments exploiting the interaction between cdc37 and a CDK, it will be understood that similar embodiments can be generated using, for example, an erk polypeptide, such as erk1 or erk2. The purification, cloning and sequence of, for example, erk1 and erk2 are provided in the art (see, for example, Boulton et al. (1991) *Cell* 663–675; Boulton et al. (1990) *Science* 249:64–67; and Boulton et al. (1991) *Biochemistry* 30:278–286), as well as described in the appended examples.

A variety of assay formats will suffice and, in light of the present disclosure, those not expressly described herein will nevertheless be comprehended by one of ordinary skill in the art. Agents to be tested for their ability to act as cdc37 inhibitors can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide, oligonucleotide, or analog thereof, having a molecular weight of less than about 2,000 daltons.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity between cdc37 and other proteins, or in changes in a property of the molecular target for cdc37 binding. Accordingly, in an exemplary screening assay of the present invention, the compound of interest is contacted with an isolated and purified cdc37 polypeptide which is ordinarily capable of binding CDK4. To the mixture of the compound and cdc37 polypeptide is then added a composition containing a CDK4 polypeptide. Detection and quantification of CDK4/cdc37 complexes provides a means for determining the compound's efficacy at inhibiting (or potentiating) complex formation between the CDK4 and cdc37 polypeptides. The efficacy of the compound can be assessed by generating dose response curves from data obtained using various concentrations of the test compound. Moreover, a control assay can also be performed to provide a baseline for comparison. In the control assay, isolated and purified CDK4 is added to a composition containing the cdc37 protein, and the formation of CDK4/cdc37 complex is quantitated in the absence of the test compound. It will be understood that, in general, the order in which the reactants may be admixed can be varied, and can be admixed simultaneously. Moreover, CDK4 can be substituted with other proteins to which cdc37 binds, as a complex by immunoprecipitation of cdc37 by anti-cdc37 antibodies, such as a protein having a molecular weight of approximately 40 kd, 42 kd, 95 kd, 107 kd and 117 kd.

Complex formation between the cdc37 polypeptide and target polypeptide may be detected by a variety of techniques. For instance, modulation of the formation of complexes can be quantitated using, for example, detectably labelled proteins such as radiolabelled (e.g. $^{32}$P, $^{35}$S, $^{14}$C or $^{3}$H), fluorescently labelled (e.g. FITC), or enzymatically labelled cdc37 or CDK4 polypeptides, by immunoassay, or by chromatographic detection. The use of enzymatically labeled CDK4 will, of course, generally be used only when enzymatically inactive portions of CDK4 are used, as each protein can possess a measurable intrinsic activity which can be detected.

Typically, it will be desirable to immobilize either the cdc37 or the CDK4 polypeptide to facilitate separation of cdc37/CDK4 complexes from uncomplexed forms of one or both of the proteins, as well as to accommodate automation of the assay. Binding of CDK4 to cdc37, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/cdc37 (GST/cdc37) fusion proteins can be adsorbed onto glutathione sepharose beads (Sigma Chemical, St. Louis, Mo.) or glutathione derivatized microtitre plates, which are then combined with the CDK4 polypeptide, e.g. an $^{35}$S-labeled CDK4 polypeptide, and the test compound, and the mixture incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the beads are washed to remove any unbound CDK4 polypeptide, and the matrix immobilized radiolabel determined directly (e.g. beads placed in scintilant), or in the supernatant after the cdc37/CDK4 complexes are subsequently dissociated. Alternatively, the complexes can dissociated from the matrix, separated by SDS-PAGE, and the level of CDK4 polypeptide found in the bead fraction quantitated from the gel using standard electrophoretic techniques such as described in the appended examples.

Other techniques for immobilizing proteins on matrices are also available for use in the subject assay. For instance, either of the cdc37 or CDK4 proteins can be immobilized utilizing conjugation of biotin and streptavidin. For instance, biotinylated cdc37 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the cdc37 but which do not interfere with CDK4 binding can be derivatized to the wells of the plate, and the cdc37 trapped in the wells by antibody conjugation. As above, preparations of a CDK4 polypeptide and a test compound are incubated in the cdc37-presenting wells of the plate, and the amount of cdc37/CDK4 complex trapped in the well can be quantitated. Exemplary methods for detecting such complexes, in addition to those described above for the GST-immobilized complexes, include immunodetection of complexes using antibodies reactive with the CDK4 polypeptide, or which are reactive with the cdc37 protein and compete for binding with the CDK4 polypeptide; as well as enzyme-linked assays which rely on detecting an enzymatic activity associated with the CDK4 polypeptide, either intrinsic or extrinsic activity. In the instance of the latter, the enzyme can be chemically conjugated or provided as a fusion protein with a CDK4 polypeptide. To illustrate, the CDK4 polypeptide can be chemically cross-linked or genetically fused with horseradish peroxidase, and the amount of CDK4 polypeptide trapped in the complex can be assessed with a chromogenic substrate of the enzyme, e.g. 3,3'-diamino-benzadine terahydrochloride or 4-chloro-1-napthol. Likewise, a fusion protein comprising the CDK4 polypeptide and glutathionc-S-transferase can be provided, and complex formation quantitated by detecting the GST activity using 1-chloro-2,4-dinitrobenzene (Habig et al (1974) *J Biol Chem* 249:7130). Direct detection of the kinase activity (intrinsic) of CDK4 can be provided using substrates known in the art, e.g., histone H1 or Rb. For instance, the ability of cdc37 to facilitate formation of an active CDK4/cyclinD 1 complex can be assessed by detecting the activation of immobilzed CDK4 after treatment with cdc37, a cyclin, and a cell lysate providing a CDK acitivating kinase (CAK).

For processes which rely on immunodetection for quantitating one of the proteins trapped in the complex, antibodies against the protein, such as either anti-CDK4 or anti-cdc37 antibodies, can be used. Alternatively, the protein to be detected in the complex can be "epitope tagged" in the form of a fusion protein which includes, in addition to the CDK4 polypeptide or cdc37 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Moreover, the subject cdc37 polypeptides can be used to generate an interaction trap assay, as described in the examples below (see also, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696), for subsequently detecting agents which disrupt binding of cdc37 to a CDK or other cell-cycle regulatory protein, e.g. Src or p53.

The interaction trap assay relies on reconstituting in vivo a functional transcriptional activator protein from two separate fusion proteins, one of which comprises the DNA-binding domain of a transcriptional activator fused to a CDK, such as CDK4. The second fusion protein comprises a transcriptional activation domain (e.g. able to initiate RNA polymerase transcription) fused to a cdc37 polypeptide. When the CDK4 and cdc37 domains of each fusion protein interact, the two domains of the transcriptional activator protein are brought into sufficient proximity as to cause transcription of a reporter gene. By detecting the level of transcription of the reporter, the ability of a test agent to inhibit (or potentiate) binding of cdc37 to CDK4 can be evaluated.

In an illustrative embodiment, *Saccharomyces cerevisiae* YPB2 cells are transformed simultaneously with a plasmid encoding a GAL4db-CDK4 fusion and with a plasmid encoding the GAL4ad domain fused to a cdc37. Moreover, the strain is transformed such that the GAL4-responsive promoter drives expression of a phenotypic marker. For example, the ability to grow in the absence of histidine can depends on the expression of the HIS3 gene. When the HIS3 gene is placed under the control of a GAL4-responsive promoter, relief of this auxotrophic phenotype indicates that a functional GAL4 activator has been reconstituted through the interaction of CDK4 and the cdc37. Thus, a test agent able to inhibit cdc37 interaction with CDK4 will result in yeast cells unable to growth in the absence of histidine. Alternatively, the phenotypic marker (e.g. instead of the HIS3 gene) can be one which provides a negative selection (e.g., are cytotoxic) when expressed such that agents which disrupt CDK4/cdc37 interactions confer positive growth selection to the cells.

In yet another embodiment, a mammalian cdc37 gene can be used to rescue a yeast cell having a defective Cdc37 gene, such as the temperature sensitive mutant (Cdc37$^{TS}$; see Reed (1980) *Genetics* 95:561–577; and Reed et al. (1985) *CSH Symp Quant Biol* 50:627–634). For example, a humanized yeast can be generated by amplifying the coding sequence of the human cdc37 clone, and subcloning this sequence into a vector which contains the yeast GAL promoter and ACT1 termination sequences flanking the cdc37 coding sequences. This plasmid can then be used to transform a Cdc37$^{TS}$ mutant (Gietz et al. (1992) *Nuc Acid Res* 20:1425). To assay growth rates, cultures of the transformed cells can be grown at 37° C. (an impermissive temperature for the TS mutant) in media supplemented with galactose. Turbidity measurements, for example, can be used to easily determine the growth rate. At the non-permissive temperature, growth of the yeast cells becomes dependent upon expression of the human cdc37 protein. Accordingly, the humanized yeast cells can be utilized to identify compounds which inhibit the action of the human cdc37 protein. It is also deemed to be within the scope of this invention that the humanized yeast cells of the present assay can be generated so as to comprise other human cell-cycle proteins. For example, human CDKs and human cyclins can also be expressed in the yeast cell. To illustrate, a triple cln deletion mutant of *S. Cerevisae* which is also conditionally deficient in cdc28 (the budding yeast equivalent of cdc2) can be rescued by the co-expression of a human cyclin D1 and human CDK4, demonstrating that yeast cell-cycle machinery can be at least in part replaced with corresponding human regulatory proteins. Roberts et al. (1993) PCT Publication Number WO 93/06123. In this manner, the reagent cells of the present assay can be generated to more closely approximate the natural interactions which the mammalian cdc37 protein might experience.

Furthermore, certain formats of the subject assays can be used to identify drugs which inhibit proliferation of yeast cells or other lower eukaryotes, but which have a substantially reduced effect on mammalian cells, thereby improving therapeutic index of the drug as an anti-mycotic agent. For instance, in one embodiment, the identification of such compounds is made possible by the use of differential screening assays which detect and compare drug-mediated disruption of binding between two or more different types of cdc37/CDK complexes. Differential screening assays can be used to exploit the difference in drug-mediated disruption of human CDK/cdc37 complexes and yeast CDC2/Cdc37 complexes in order to identify agents which display a statistically significant increase in specificity for disrupting the yeast complexes relative to the human complexes. Thus, lead compounds which act specifically to inhibit proliferation of pathogens, such as fungus involved in mycotic infections, can be developed. By way of illustration, the present assays can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise comparing the relative effectiveness of a test compound on mediating disruption of a human CDK4/cdc37 complex with its effectiveness towards disrupting the equivalent complexes formed from genes cloned from yeast selected from the group consisting of *Candida albicans, Candida stellatoidea, Candida tropicalis, Candida parapsilosis, Candida krusei, Candida pseudotropicalis, Candida quillermondii*, or *Candida rugosa*. Likewise, the present assay can be used to identify anti-fungal agents which may have therapeutic value in the treatment of aspergillosis by making use of an interaction trap assays derived from CDK and Cdc37 genes cloned from yeast such as *Aspergillus fumigatus, Aspergillus flavus, Aspergillus niger, Aspergillus nidulans*, or *Aspergillus terreus*. Where the mycotic infection is mucormycosis, the complexes can be derived from yeast such as *Rhizopus arrhizus, Rhizopus oryzae, Absidia corymbifera, Absidia ramosa*, or *Mucor pusillus*. Sources of other Cdc37-containing complexes for comparison with a human CDK/cdc37 complex includes the pathogen *Pneumocystis carinii*.

EXEMLIFICATION

The invention now being generally described, it will be more readily understood by reference to the following examples which are included merely for purposes of illustration of certain aspects and embodiments of the present invention, and are not intended to limit the invention.

Manipulation of *E coli*, yeast and DNA was by standard methods

Interaction Trap

A general transcription-based selection for protein-protein interactions was used to isolate cDNA which encode proteins able to bind to CDK4. Development of the "interaction trap assay" or ITS, is described in, for example, Gyuris et al. (1993) *Cell* 75:791–803; Chien et al. (1991) *NAS* 88:9578–9582; Dalton et al. (1992) *Cell* 68:597–612; Durfee et al. (1993) *Genes Dev* 7:555–569; Vojteck et al. (1993) *Cell* 74:205–214; Fields et al. (1989) *Nature* 340:245–246; and U.S. Pat. No. 5,283,173). As carried out in the present invention, the interaction trap comprises three different components: a fusion protein that contains the LexA DNA-binding domain and that is known to be transcriptionally inert (the "bait"); reporter genes that have no basal transcription and whose transcriptional regulatory sequences are dependent on binding of LexA; and the proteins encoded by an expression library, which are expressed as chimeras and whose amino termini contrain an activation domain and other useful moieties (the "fish"). Briefly, baits were produced constitutively from a 211 HIS3+ plasmid under the control of the ADH1 promoter and contained the LexA carboxy-terminal oligomerization region. Baits were made in pLexA(1-202)+1 (described in Ruden et al. *Nature* (1991) 350:250–252; and Gyuris et al. *Cell* (1993) 75:791–803) after PCR amplification of the bait coding sequences from the second amino acid to the stop codon, except for p53 where the bait moiety starts at amino acid 74. Using the PCR primers described in below, CDK2 and CDK3 were cloned as EcoR1-BamH1 fragments; CDK4, cyclin D1, cyclin D2, Cyclin E as EcoR1-Sal1 fragments; CDK5, CDK6, Cdi1 as EcoR1-Xho1 fragments; and retinoblastoma (pRb), mutRb (Δ702–737), p53 and cyclin C as BamH1-Sal1 fragments. When EcoR1 is used, there are two amino acid inserted (EF) between the last amino acid of LexA and the bait moieties. BamH1 fusion results in five amino acid insertion (EFPGI) between LexA and the fused protein.

PCR primers

CDK2:
5'-GGCGGCCGCGAATTCGAGAACTTCCAAAAGGTGGAAAAG-3' (SEQ ID NO 3)
5'-GCGGCCGCGGATCCAGGCTATCAGAGTCGAAGATGGGGTAC-3' (SEQ ID NO: 4)

CDK3:
5'-GCGGCCGCGAATTCGAAGCTGGAGGAGCAACCGGGAGC-3' (SEQ ID NO: 5)
5'-GCGGCCGCGGATCCTCAATGGCGGAATCGCTGCAGCAC-3' (SEQ ID NO: 6)

CDK5:
5'-GCGGCGGCGTCGACCAGAAATACGAGAAACTGGAAAAG-3' (SEQ ID NO. 7)
5'-GCGGCGGCGTCGACCGGGGCCTAGGGCGGACAGAAGTC-3' (SEQ ID NO. 8)

CDK6:
5'-GCGGCCGCGAATTCGAGAAGGACGGCCTGTGCCGCGCT-3' (SEQ ID NO: 9)
5'-GCGGCGGCCTCGAGGAGGCCTCAGGCTGTATTCAGCTC-3' (SEQ ID NO: 10)

Cyclin C:
5'-GGCCGGCCGGGATCCTTGTCGCTCCGCGGCTGCTCCGGCTG-3' (SEQ ID NO. 11)
5'-GCGGCCGCGTCGACGTTTTAAGATTGGCTGTAGCTAGAG-3' (SEQ ID NO. 12)

-continued

Cyclin D1:
5'-GGCCGGCCGGAATTCGAACACCAGCTCCTGTGCTGCGAAG-3' (SEQ ID NO: 13)
5'-GCGGCCGCGTCGACGCGCCCTCAGATGTCCACGTCCCGC-3' (SEQ ID NO: 14)

Cyclin D2:
5'-GCGGCGGCGAATTCGAGCTGCTGTGCCACGAGGTGGAC-3' (SEQ ID NO. 15)
5'-GCGGCGGCGAATTCGAGCTGCTGTGCCACGAGGTGGAC-3' (SEQ ID NO. 16)

Cyclin E:
5'-GGCCGGCCGGAATTCAAGGAGGACGGCGGCGCGGAGTTC-3' (SEQ ID NO. 17)
5'-GCGGCCGCGTCGACGGGTGGTCACGCCATTTCCGGCCCG-3' (SEQ ID NO. 18)

Cdi1:
5'-GCGGCCGCGAATTCAAGCCGCCCAGTTCAATACAAACAAG-3' (SEQ ID NO. 19)
5'-GCGGCCGCCTCGAGATTCCTTTATCTTGATACAGATCTTG-3' (SEQ ID NO: 20)

Rb:
5'-GCGGCCGCGGATCCAGCCGCCCAAAACCCCCCGAAAAACG-3' (SEQ ID NO: 21)
5'-GCGGCCGCGAATTCCTCGAGCTCATTTCTCTTCCTTGTTTGAGG-3' (SEQ ID NO: 22)

p53:
5'-GCGGCCGCGGATCCAAGCCCCTGCACCAGCAGCTCCTACA-3' (SEQ ID NO: 23)
5'-GCGGCCGCGTCGACTCAGTCTGAGTCAGGCCCTTCTGT-3' 9SEQ ID NO: 24)

Reporters

The LexAop-LEU2 construction replaced the yeast chromosomal LEU2 gene. The other reporter, pRB1840, one of a series of LexAop-GAL1-lacZ genes (Brent et al. (1985) *Cell* 43:729–736; Kamens et al. (1990) *Mol Cell Biol* 10:2840–2847), was carried on a 2μ plasmid. Basal reporter transcription was extremely low, presumably owing both to the removal of the entire upstream activating sequence from both reporters and to the fact that LexA operators introduced into yeast promoters decrease their transcription (Brent and Ptashne (1984) *Nature* 312:612–615). Reporters were chosen to differ in sensitivity. The LEU2 reporter contained three copies of the high affinity LexA-binding site found upstream of *E. coli* colE1, which presumably bind a total of six dimers of the bait. In contrast, the lacZ gene contained a single lower affinity operator that binds a single dimer of the bait. The operators in the LEU2 reporter were closer to the transcription start point than they were in the lacZ reporter. These differences in the number, affinity, and operator position all contribute to that fact that the LEU2 reporter is more sensitive than the lacZ gene.

Expression Vectors and Library

Library proteins were expressed from pJG4-5, a member of a series of expression plasmids designed to be used in the interaction trap and to facilitate analysis of isolated proteins. These plasmids carry the 2μ replicator and the TRP1 marker. pJG4-5, shown in FIG. 1, directs the synthesis of fusion proteins. Proteins expressed from this vector possess the following features: galactose-inducible expression so that their synthesis is conditional, an epitope tag to facilitate detection, a nuclear localization signal to maximize intranuclear concentration to increase selection sensitivity, and an activation domain derived from *E. coli* (Ma and Ptashne (1987) *Cell* 57:113–119), chosen because its activity is not subject to known regulation by yeast proteins and because it is weak enough to avoid toxicity (Gill and Ptashne (1988) *Nature* 334:721–724; Berger et al. (1992) *Cell* 70:251–265) that might restrict the number or type of interacting proteins recovered. We introduced EcoRI-XhoI cDNA-containing fragments, which were generated from a quiescent normal fibroblast line (WI38), into the pJG4-5 plasmid.

CDK4 Interaction Trap

We began with yeast cells which contained LexAop-LEU2 and LexAop-lacZ reporters and the LexA-CDK4 bait.

We introduced the WI38 cDNA library (in pJG4-5) into this strain. We recovered a number of transformants on glucose Ura⁻ His⁻ Trp⁻ plates, scraped them, suspended them in approximately 20 ml of 65% glycerol, 10 mM Tris-HCI (pH 7.5), 10 mM MgCl$_2$, and stored the cells in 1 ml aliquots at –80° C. We determined plating efficiency on galactose Ura⁻ His⁻ Trp⁻ after growing 50 μl of cell suspension for 5 hr in 5 ml of YP medium, 2% galactose. For the selection, about 2×10⁷ galactose-viable cells were plated on four standard circular 10 cm galactose Ura⁻ His⁻ Trp⁻ Leu⁻ plates after galactose induction. After 4 days at 30° C., LEU+ colonies appeared and were collected on glucose Ura⁻His⁻ Trp⁻ master plates and retested on glucose Ura⁻ His⁻ Trp⁻ Leu⁻, galactose Ura⁻ His⁻ Trp⁻ Leu⁻, glucose X-Gal Ura⁻ His⁻ Trp⁻, and galactose X⁻ Gal Ura⁻ His⁻ Trp⁻ plates. Of these, plasmid DNAs were rescued from colonies which showed galactose-dependent growth on Leu⁻ media and galactose-dependent blue color on X-Gal medium (Hoffman and Winston, (1987) *Gene* 57:267–272), introduced into *E. coli* KC8, and transformants collected on Trp⁻ ampicillin plates.

We classified library plasmids by restriction pattern on 1.8% agarose, 0.5×Tris-borate-EDTA gels after digestion with EcoRI and XhoI and either AluI or HaeIII. Clones from each class were sequenced, including a class which gave rise to the human cdc37 clone described herein.

Furthermore, we reintroduced the cdc37 clone that contained the longest fragment of that cDNA (e.g. the complete coding region) into EGY48 derivatives that contained a panel of different baits, e.g. other CDKs, cyclins, p53, Rb, etc. The human cdc37 clone displayed different binding affinities for other cell-cycle regulatory proteins. In particular, cdc37 demonstrated binding to CDK4, and to a lesser extent, CDK5, as well as RB and p53. The cdc37 protein did not display any binding in the ITS to CDK2 or CDK3, nor did it appear to bind to cdi1 or any of cyclin C, D1, D2 or E. This finding is significant for a number of reasons. For example, the cdc37/CDK4 interaction is desirable as a therapeutic target for drug design, in that the selectivity of that interaction relative to cdc37 interaction with other cell-cycle regulatory proteins represents the opportunity to obtain drugs with excellent therapeutic indexes.

Purification of cdc37 Associated Kinases from Mammalian Cell Extracts

Gst-cdc37 protein was bound to glutathione-Sepharose and incubated with HeLa cell lysates. The unbound proteins were washed extensively and the cdc37 bound proteins were eluted by a NaCl salt gradient. The eluted fractions were assayed for kinase activity using Gst-cdc37 as a substrate. Kinase activity that phosphorylated cdc37 was present in fractions eluted between 150–350mM NaCl.

The fractions that contained kinase activity were collected, and an aliquot of the pool was run on SDS/PAGE that contained cdc37 protein in the gel. Unfractioned Hela extracts were used as a control. After the renaturation of the separated proteins, in gel kinases assays were performed and the active kinase bands detected by autoradiography. Five bands were identified as active by this assay, which bainds are characterized by molecular weights of 115–120 kd, 105–110 kd, 95 kd, 42 kd and 40 kd, and were identical in the pool and in the control Hela extracts.

The presence of the 40 and 42 kd doublet was reminiscent of Erk1 and Erk2, so this possibility was explored. An aliquot of the pool and unfractioned Hela extract were run on SDS/PAGE, transferred to filters, and blotted with an antibody that recognized Erk1 and Erk2. The same molecular weight bands were detected by immunoblotting in both the pool and the control Hela extract, indicating that Erk1 and Erk2 associate with cdc37.

Consistent with this, Erk1 and Erk2 immunoprecipitated from human cells can phosphorylate cdc37 in vitro.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A substantially pure cdc37 polypeptide, which polypeptide comprises a cdc37 amino acid sequence at least 80 percent identical to the amino acid sequence designated by SEQ ID No. 2, or a portion thereof, and which polypeptide or a portion thereof specifically binds to at least one of a cyclin-dependent kinase (CDK) and a extracellular-signal regulated kinase (erk).

2. The cdc37 polypeptide of claim 1, wherein said CDK is a G₁ phase CDK.

3. The cdc37 polypeptide of claim 2, wherein said CDK is CDK4.

4. The cdc37 polypeptide of claim 1, wherein said erk is selected from the group consisting of erk1 and erk2.

5. The cdc37 polypeptide of claim 1, which polypeptide modulates at least one of proliferation, differentiation and survival of a cell.

6. The cdc37 polypeptide of claim 5, which polypeptide stimulates activation of a kinase activity of said CDK.

7. The cdc37 polypeptide of claim 5, which polypeptide antagonizes activation of a kinase activity of said CDK.

8. The cdc37 polypeptide of claim 1, which polypeptide binds to a p53 protein.

9. The cdc37 polypeptide of claim 1, which cdc37 amino acid sequence is at least 98 percent identical to the amino acid sequence designated by SEQ ID No. 2.

10. The cdc37 polypeptide of claim 1, which cdc37 amino acid sequence is at least 90 percent identical to the amino acid sequence designated by SEQ ID No. 2.

11. The cdc37 polypeptide of claim 1, which cdc37 amino acid sequence is at least 95 percent identical to the amino acid sequence designated by SEQ ID No. 2.

12. The cdc37 polypeptide of claim 1, which cdc37 amino acid sequence is designated by SEQ ID No. 2.

13. The cdc37 polypeptide of claim 1, 3, 9, 10, or 11, which cdc37 amino acid sequence is encoded by a nucleic acid which hybridizes under conditions of high stringency to a nucleic acid sequence of SEQ ID No. 1.

14. The cdc37 polypeptide of claim 1, 3, 9, 10, or 11, which cdc37 amino acid sequence is encoded by a naturally occurring cdc37 gene of a mammal.

15. The cdc37 polypeptide of claim 14, which cdc37 gene is a human cdc37 gene.

16. The cdc37 polypeptide of claim 1, 3, 9, 10 or 11, which polypeptide is a fusion protein.

17. The cdc37 polypeptide of claim 13, wherein said fusion protein includes a second polypeptide sequence which is a detectable label for detecting the presence of said fusion protein and/or is a matrix-binding domain for immobilizing said fusion protein.

18. The cdc37 polypeptide of claim 13, wherein said fusion protein includes a second polypeptide sequence possessing an enzymatic activity.

19. The cdc37 polypeptide of any of claims 1, 3, 9, 10, or 11, wherein the polypeptide is purified to at least 80% by dry weight.

20. A purified protein complex consisting essentially of a cdc37 polypeptide including a naturally occurring cdc37 amino acid sequence, and one or more proteins which specifically bind to the cdc37 protein.

21. The protein complex of claim 20, including a cyclin dependent kinase (cdk).

22. The protein complex of claim 21, wherein the cdk is cdk4.

23. The protein complex of claim 20, including an extracellular-signal regulated kinase (erk).

24. The protein complex of claim 23, wherein the erk is selected from the group consisting of erk1 and erk2.

25. The protein complex of claim 20, including one or proteins having apparent molecular weights by SDS/PAGE of about 115 kd, 105 kd, 95 kd, 42 kd and 40 kd.

26. The protein complex of claim 20, 22 or 23, which cdc37 amino acid sequence is encoded by a naturally occurring cdc37 gene of a mammal.

27. The protein complex of claim 26, which cdc37 gene is a human cdc37 gene.

28. The protein complex of any of claims 20, 22 or 23, wherein the protein complex is purified to at least 80% by dry weight.

29. A fusion protein comprising a a cdc37 amino acid sequence which is at least 80 percent identical to the amino acid sequence designated by SEQ ID No. 2, or a portion thereof, which specifically binds to at least one of a cyclin-dependent kinase (CDK) and a extracellular-signal regulated kinase (erk).

30. The fusion protein of claim 29, wherein said CDK is CDK4.

31. The fusion protein of claim 29, wherein said erk is selected from the group consisting of erk1 and erk2.

32. The fusion protein of claim 29, which cdc37 amino acid sequence is at least 90 percent identical to the amino acid sequence designated by SEQ ID No. 2.

33. The fusion protein of claim 29, which cdc37 amino acid sequence is at least 98 percent identical to the amino acid sequence designated by SEQ ID No. 2.

34. The fusion protein of claim 29, which cdc37 amino acid sequence is encoded by a nucleic acid which hybridizes under conditions of high stringency to a nucleic acid sequence of SEQ ID No. 1.

35. The fusion protein of claim 29, wherein said fusion protein includes a second polypeptide sequence which is a detectable label for detecting the presence of said fusion protein and/or is a matrix-binding domain for immobilizing said fusion protein.

36. The fusion protein of claim 35, wherein said fusion protein includes a second polypeptide sequence possessing an enzymatic activity.

37. A purified preparation of a cdc37 polypeptide, which polypeptide comprises a naturally occurring cdc37 amino acid sequence from a mammal which specifically binds to at least one of a cyclin-dependent kinase (CDK) and a extracellular-signal regulated kinase (erk).

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 1603 base pairs
( B ) TYPE: nucleic acid
( C ) STRANDEDNESS: both
( D ) TOPOLOGY: linear ( i i ) MOLECULE TYPE: cDNA ( i x ) FEATURE:
( A ) NAME/KEY: CDS
( B ) LOCATION: 43..1161

( x i ) SEQUENCE DESCRIPTION: SEQ ID NO:1:

```
CGCCGCCACC CGAGCCGGAG CGGGTTGGGC CGCCAAGGCA AG ATG GTG GAC TAC                54
                                                Met Val Asp Tyr
                                                  1

AGC GTG TGG GAC CAC ATT GAG GTG TCT GAT GAT GAA GAC GAG ACG CAC              102
Ser Val Trp Asp His Ile Glu Val Ser Asp Asp Glu Asp Glu Thr His
  5              10                  15                      20

CCC AAC ATC GAC ACG GCC AGT CTC TTC CGC TGG CGG CAT CAG GCC CGG              150
Pro Asn Ile Asp Thr Ala Ser Leu Phe Arg Trp Arg His Gln Ala Arg
                 25                  30                  35

GTG GAA CGC ATG GAG CAG TTC CAG AAG GAG AAG GAG GAA CTG GAC AGG              198
Val Glu Arg Met Glu Gln Phe Gln Lys Glu Lys Glu Glu Leu Asp Arg
             40                  45                  50

GGC TGC CGC GAG TGC AAG CGC AAG GTG GCC GAG TGC CAG AGG AAA CTG              246
Gly Cys Arg Glu Cys Lys Arg Lys Val Ala Glu Cys Gln Arg Lys Leu
         55                  60                  65

AAG GAG CTG GAG GTG GCC GAG GGC GGC AAG GCA GAG CTG GAG CGC CTG              294
Lys Glu Leu Glu Val Ala Glu Gly Gly Lys Ala Glu Leu Glu Arg Leu
     70                  75                  80

CAG GCC GAG AGC ACA GCA GCT GCG CAA GGA GGA GCG GAG CTG GGA GCA              342
Gln Ala Glu Ser Thr Ala Ala Ala Gln Gly Gly Ala Glu Leu Gly Ala
 85                  90                  95                 100

GAA GCT GGA GGG AGA TGC GCA AGA AGG AGA AGA GCA TGC CCT GGC AAC              390
Glu Ala Gly Gly Arg Cys Ala Arg Arg Arg Arg Ala Cys Pro Gly Asn
                105                 110                 115
```

-continued

| | | | | | | | | | | | | | | | | |
|---|---|---|---|---|---|---|---|---|---|---|---|---|---|---|---|---|
| GTG | GAC | ACG | CTC | AGC | AAA | GAC | GGC | TTC | AGC | AAG | AGC | ATG | GTA | AAT | ACC | 438 |
| Val | Asp | Thr | Leu | Ser | Lys | Asp | Gly | Phe | Ser | Lys | Ser | Met | Val | Asn | Thr | |
| | | | 120 | | | | | 125 | | | | | 130 | | | |
| AAG | CCC | GAG | AAG | ACG | GAG | GAG | GAC | TCA | GAG | GAG | GTG | AGG | GAG | CAG | AAA | 486 |
| Lys | Pro | Glu | Lys | Thr | Glu | Glu | Asp | Ser | Glu | Glu | Val | Arg | Glu | Gln | Lys | |
| | | | 135 | | | | | 140 | | | | | 145 | | | |
| CAC | AAG | ACC | TTC | GTG | GAA | AAA | TAC | GAG | AAA | CAG | ATC | AAG | CAC | TTT | GGC | 534 |
| His | Lys | Thr | Phe | Val | Glu | Lys | Tyr | Glu | Lys | Gln | Ile | Lys | His | Phe | Gly | |
| | | 150 | | | | | 155 | | | | | 160 | | | | |
| ATG | CTT | CGC | CGC | TGG | GAT | GAC | AGC | CAC | AAG | TAC | CTG | TCA | GAC | AAC | GTC | 582 |
| Met | Leu | Arg | Arg | Trp | Asp | Asp | Ser | His | Lys | Tyr | Leu | Ser | Asp | Asn | Val | |
| 165 | | | | | 170 | | | | | 175 | | | | | 180 | |
| CAC | CTG | GTG | TGC | GAG | GAG | ACA | GCC | AAT | TAC | CTG | GTC | ATT | TGG | TGC | ATT | 630 |
| His | Leu | Val | Cys | Glu | Glu | Thr | Ala | Asn | Tyr | Leu | Val | Ile | Trp | Cys | Ile | |
| | | | | | | 185 | | | | | 190 | | | | | 195 |
| GAC | CTA | GAG | GTG | GAG | GAG | AAA | TGT | GCA | CTC | ATG | GAG | CAG | GTG | GCC | CAC | 678 |
| Asp | Leu | Glu | Val | Glu | Glu | Lys | Cys | Ala | Leu | Met | Glu | Gln | Val | Ala | His | |
| | | | | 200 | | | | | 205 | | | | | 210 | | |
| CAG | ACA | ATC | GTC | ATG | CAA | TTT | ATC | CTG | GAG | CTG | GCC | AAG | AGC | CTA | AAG | 726 |
| Gln | Thr | Ile | Val | Met | Gln | Phe | Ile | Leu | Glu | Leu | Ala | Lys | Ser | Leu | Lys | |
| | | 215 | | | | | 220 | | | | | 225 | | | | |
| GTG | GAC | CCC | CGG | GCC | TGC | TTC | CGG | CAG | TTC | TTC | ACT | AAG | ATT | AAG | ACA | 774 |
| Val | Asp | Pro | Arg | Ala | Cys | Phe | Arg | Gln | Phe | Phe | Thr | Lys | Ile | Lys | Thr | |
| | 230 | | | | | 235 | | | | | 240 | | | | | |
| GCC | GAT | CGC | CAG | TAC | ATG | GAG | GGC | TTC | AAC | GAC | GAG | CTG | GAA | GCC | TTC | 822 |
| Ala | Asp | Arg | Gln | Tyr | Met | Glu | Gly | Phe | Asn | Asp | Glu | Leu | Glu | Ala | Phe | |
| 245 | | | | | 250 | | | | | 255 | | | | | 260 | |
| AAG | GAG | CGT | GTG | CGG | GGC | CGT | GCC | AAG | CTG | CGC | ATC | GAG | AAG | GCC | ATG | 870 |
| Lys | Glu | Arg | Val | Arg | Gly | Arg | Ala | Lys | Leu | Arg | Ile | Glu | Lys | Ala | Met | |
| | | | | 265 | | | | | 270 | | | | | 275 | | |
| AAG | GAG | TAC | GAG | GAG | GAG | GAG | CGC | AAG | AAG | CGG | CTC | GGC | CCC | GGC | GGC | 918 |
| Lys | Glu | Tyr | Glu | Glu | Glu | Glu | Arg | Lys | Lys | Arg | Leu | Gly | Pro | Gly | Gly | |
| | | | 280 | | | | | 285 | | | | | 290 | | | |
| CTG | GAC | CCC | GTC | GAG | GTC | TAC | GAG | TCC | CTC | CCT | GAG | GAA | CTC | CAG | AAG | 966 |
| Leu | Asp | Pro | Val | Glu | Val | Tyr | Glu | Ser | Leu | Pro | Glu | Glu | Leu | Gln | Lys | |
| | | 295 | | | | | 300 | | | | | 305 | | | | |
| TGC | TTC | GAT | GTG | AAG | GAC | GTG | CAG | ATG | CTG | CAG | GAC | GCC | ATC | AGC | AAG | 1014 |
| Cys | Phe | Asp | Val | Lys | Asp | Val | Gln | Met | Leu | Gln | Asp | Ala | Ile | Ser | Lys | |
| 310 | | | | | 315 | | | | | 320 | | | | | | |
| ATG | GAC | CCC | ACC | GAC | GCA | AAG | TAC | CAC | ATG | CAG | CGC | TGC | ATT | GAC | TCT | 1062 |
| Met | Asp | Pro | Thr | Asp | Ala | Lys | Tyr | His | Met | Gln | Arg | Cys | Ile | Asp | Ser | |
| 325 | | | | | 330 | | | | | 335 | | | | | 340 | |
| GGC | CTC | TGG | GTC | CCC | AAC | TCT | AAG | GCC | AGC | GAG | GCC | AAG | GAG | GGA | GAG | 1110 |
| Gly | Leu | Trp | Val | Pro | Asn | Ser | Lys | Ala | Ser | Glu | Ala | Lys | Glu | Gly | Glu | |
| | | | | 345 | | | | | 350 | | | | | 355 | | |
| GAG | GCA | GGT | CCT | GGG | GAC | CCA | TTA | CTG | GAA | GCT | GTT | CCC | AAG | ACG | GGG | 1158 |
| Glu | Ala | Gly | Pro | Gly | Asp | Pro | Leu | Leu | Glu | Ala | Val | Pro | Lys | Thr | Gly | |
| | | | 360 | | | | | 365 | | | | | 370 | | | |

| | |
|---|---|
| CGA TGAGAAGGAT GTCAGTGTGT GACCTGCCCC AGCTACCACC GCCACCTGCT | 1211 |
| Arg | |
| TCCAGGCCCC TATGTGCCCC CTTTTCAAGA AAACAAGATA GATGCCATCT CGCCCGCTCC | 1271 |
| TGACTTCCTC TACTTGCGCT GCTCGGCCCA GCCTGGGGGG CCCGCCCAGC CCTCCCTGGC | 1331 |
| CTCTCCACTG TCTCCACTCT CCAGCGCCCA ATCAAGTCTC TGCTTTGAGT CAAGGGGCTT | 1391 |
| CACTGCCTGC AGCCCCCCAT CAGCATTATG CCAAAGGCCC GGGGGTCCGG GGAAGGGCAG | 1451 |
| AGGTCACCAG GCTGGTCTAC CAGGTAGTTG GGAGGGTCC CCAACCAAGG GGCCGGCTCT | 1511 |
| CGTCACTGGG CTCTGTTTTC ACTGTTCGTC TGCTGTCTGT GTCTTCTAAT TGGCAAACAA | 1571 |
| CAATGATCTT CCAATAAAAG ATTTCAGATG CC | 1603 |

( 2 ) INFORMATION FOR SEQ ID NO:2:

( i ) SEQUENCE CHARACTERISTICS:
        ( A ) LENGTH: 373 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Asp Tyr Ser Val Trp Asp His Ile Glu Val Ser Asp Asp Glu
 1               5                  10                  15
Asp Glu Thr His Pro Asn Ile Asp Thr Ala Ser Leu Phe Arg Trp Arg
                 20                  25                  30
His Gln Ala Arg Val Glu Arg Met Glu Gln Phe Gln Lys Glu Lys Glu
             35                  40                  45
Glu Leu Asp Arg Gly Cys Arg Glu Cys Lys Arg Lys Val Ala Glu Cys
         50                  55                  60
Gln Arg Lys Leu Lys Glu Leu Glu Val Ala Glu Gly Gly Lys Ala Glu
 65                  70                  75                  80
Leu Glu Arg Leu Gln Ala Glu Ser Thr Ala Ala Ala Gln Gly Gly Ala
                 85                  90                  95
Glu Leu Gly Ala Glu Ala Gly Gly Arg Cys Ala Arg Arg Arg Arg Ala
                100                 105                 110
Cys Pro Gly Asn Val Asp Thr Leu Ser Lys Asp Gly Phe Ser Lys Ser
            115                 120                 125
Met Val Asn Thr Lys Pro Glu Lys Thr Glu Glu Asp Ser Glu Glu Val
    130                 135                 140
Arg Glu Gln Lys His Lys Thr Phe Val Glu Lys Tyr Glu Lys Gln Ile
145                 150                 155                 160
Lys His Phe Gly Met Leu Arg Arg Trp Asp Asp Ser His Lys Tyr Leu
                165                 170                 175
Ser Asp Asn Val His Leu Val Cys Glu Glu Thr Ala Asn Tyr Leu Val
            180                 185                 190
Ile Trp Cys Ile Asp Leu Glu Val Glu Glu Lys Cys Ala Leu Met Glu
        195                 200                 205
Gln Val Ala His Gln Thr Ile Val Met Gln Phe Ile Leu Glu Leu Ala
    210                 215                 220
Lys Ser Leu Lys Val Asp Pro Arg Ala Cys Phe Arg Gln Phe Phe Thr
225                 230                 235                 240
Lys Ile Lys Thr Ala Asp Arg Gln Tyr Met Glu Gly Phe Asn Asp Glu
                245                 250                 255
Leu Glu Ala Phe Lys Glu Arg Val Arg Gly Arg Ala Lys Leu Arg Ile
            260                 265                 270
Glu Lys Ala Met Lys Glu Tyr Glu Glu Glu Arg Lys Lys Arg Leu
        275                 280                 285
Gly Pro Gly Gly Leu Asp Pro Val Glu Val Tyr Glu Ser Leu Pro Glu
    290                 295                 300
Glu Leu Gln Lys Cys Phe Asp Val Lys Asp Val Gln Met Leu Gln Asp
305                 310                 315                 320
Ala Ile Ser Lys Met Asp Pro Thr Asp Ala Lys Tyr His Met Gln Arg
                325                 330                 335
Cys Ile Asp Ser Gly Leu Trp Val Pro Asn Ser Lys Ala Ser Glu Ala
            340                 345                 350
Lys Glu Gly Glu Glu Ala Gly Pro Gly Asp Pro Leu Leu Glu Ala Val
```

```
                355                      360                     365
Pro  Lys  Thr  Gly  Arg
          370
```

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GGCGGCCGCG AATTCGAGAA CTTCCAAAAG GTGGAAAAG                                39
```

( 2 ) INFORMATION FOR SEQ ID NO:4:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
GCGGCCGCGG ATCCAGGCTA TCAGAGTCGA AGATGGGGTA C                            41
```

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GCGGCCGCGA ATTCGAAGCT GGAGGAGCAA CCGGGAGC                                 38
```

( 2 ) INFORMATION FOR SEQ ID NO:6:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GCGGCCGCGG ATCCTCAATG GCGGAATCGC TGCAGCAC                                 38
```

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
GCGGCGGCGT CGACCAGAAA TACGAGAAAC TGGAAAAG                                 38
```

( 2 ) INFORMATION FOR SEQ ID NO:8:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCGGCGGCGT CGACCGGGGC CTAGGGCGGA CAGAAGTC        38

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GCGGCCGCGA ATTCGAGAAG GACGGCCTGT GCCGCGCT        38

( 2 ) INFORMATION FOR SEQ ID NO:10:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCGGCGGCCT CGAGGAGGCC TCAGGCTGTA TTCAGCTC        38

( 2 ) INFORMATION FOR SEQ ID NO:11:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGCCGGCCGG GATCCTTGTC GCTCCGCGGC TGCTCCGGCT G        41

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GCGGCCGCGT CGACGTTTTA AGATTGGCTG TAGCTAGAG        39

( 2 ) INFORMATION FOR SEQ ID NO:13:

( i ) SEQUENCE CHARACTERISTICS:
        ( A ) LENGTH: 40 base pairs (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:13:

GGCCGGCCGG AATTCGAACA CCAGCTCCTG TGCTGCGAAG    40

(2) INFORMATION FOR SEQ ID NO:14:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:14:

GCGGCCGCGT CGACGCGCCC TCAGATGTCC ACGTCCCGC    39

(2) INFORMATION FOR SEQ ID NO:15:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:15:

GCGGCGGCGA ATTCGAGCTG CTGTGCCACG AGGTGGAC    38

(2) INFORMATION FOR SEQ ID NO:16:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:16:

GCGGCGGCGA ATTCGAGCTG CTGTGCCACG AGGTGGAC    38

(2) INFORMATION FOR SEQ ID NO:17:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:17:

GGCCGGCCGG AATTCAAGGA GGACGGCGGC GCGGAGTTC    39

(2) INFORMATION FOR SEQ ID NO:18:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: cDNA ( x i ) SEQUENCE DESCRIPTION: SEQ ID NO:18:

GCGGCCGCGT CGACGGGTGG TCACGCCATT TCCGGCCCG        39

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GCGGCCGCGA ATTCAAGCCG CCCAGTTCAA TACAAACAAG        40

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GCGGCCGCCT CGAGATTCCT TTATCTTGAT ACAGATCTTG        40

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GCGGCCGCGG ATCCAGCCGC CCAAAACCCC CCGAAAAACG        40

( 2 ) INFORMATION FOR SEQ ID NO:22:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

GCGGCCGCGA ATTCCTCGAG CTCATTTCTC TTCCTTGTTT GAGG        44

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

GCGGCCGCGG ATCCAAGCCC CTGCACCAGC AGCTCCTACA        40

( 2 ) INFORMATION FOR SEQ ID NO:24:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GCGGCCGCGT CGACTCAGTC TGAGTCAGGC CCTTCTGT                                    38
```

( 2 ) INFORMATION FOR SEQ ID NO:25:

( i ) SEQUENCE CHARACTERISTICS:
        ( A ) LENGTH: 345 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..327

( x i ) SEQUENCE DESCRIPTION: SEQ ID NO:25:

```
AAGCTT ATG GGT GCT CCT CCA AAA AAG AAG AGA AAG GTA GCT GGT ATC               48
       Met Gly Ala Pro Pro Lys Lys Lys Arg Lys Val Ala Gly Ile
        1               5                  10

AAT AAA GAT ATC GAG GAG TGC AAT GCC ATC ATT GAG CAG TTT ATC GAC              96
Asn Lys Asp Ile Glu Glu Cys Asn Ala Ile Ile Glu Gln Phe Ile Asp
 15              20                  25                  30

TAC CTG CGC ACC GGA CAG GAG ATG CCG ATG GAA ATG GCG GAT CAG GCG             144
Tyr Leu Arg Thr Gly Gln Glu Met Pro Met Glu Met Ala Asp Gln Ala
                 35                  40                  45

ATT AAC GTG GTG CCG GGC ATG ACG CCG AAA ACC ATT CTT CAC GCC GGG             192
Ile Asn Val Val Pro Gly Met Thr Pro Lys Thr Ile Leu His Ala Gly
             50                  55                  60

CCG CCG ATC CAG CCT GAC TGG CTG AAA TCG AAT GGT TTT CAT GAA ATT             240
Pro Pro Ile Gln Pro Asp Trp Leu Lys Ser Asn Gly Phe His Glu Ile
         65                  70                  75

GAA GCG GAT GTT AAC GAT ACC AGC CTC TTG CTG AGT GGA GAT GCC TCC             288
Glu Ala Asp Val Asn Asp Thr Ser Leu Leu Leu Ser Gly Asp Ala Ser
     80                  85                  90

TAC CCT TAT GAT GTG CCA GAT TAT GCC TCT CCC GAA TTC GGCCGACTCG              337
Tyr Pro Tyr Asp Val Pro Asp Tyr Ala Ser Pro Glu Phe
 95                 100                 105

AGAAGCTT                                                                    345
```

( 2 ) INFORMATION FOR SEQ ID NO:26:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Gly Ala Pro Pro Lys Lys Lys Arg Lys Val Ala Gly Ile Asn Lys
 1               5                  10                  15

Asp Ile Glu Glu Cys Asn Ala Ile Ile Glu Gln Phe Ile Asp Tyr Leu
             20                  25                  30
```

```
Arg  Thr  Gly  Gln  Glu  Met  Pro  Met  Glu  Met  Ala  Asp  Gln  Ala  Ile  Asn
          35                       40                      45

Val  Val  Pro  Gly  Met  Thr  Pro  Lys  Thr  Ile  Leu  His  Ala  Gly  Pro  Pro
          50                  55                      60

Ile  Gln  Pro  Asp  Trp  Leu  Lys  Ser  Asn  Gly  Phe  His  Glu  Ile  Glu  Ala
 65                      70                       75                          80

Asp  Val  Asn  Asp  Thr  Ser  Leu  Leu  Leu  Ser  Gly  Asp  Ala  Ser  Tyr  Pro
                85                            90                          95

Tyr  Asp  Val  Pro  Asp  Tyr  Ala  Ser  Pro  Glu  Phe
               100                      105
```